US011160894B2

(12) United States Patent
O'Leary et al.

(10) Patent No.: US 11,160,894 B2
(45) Date of Patent: Nov. 2, 2021

(54) PERFUME EMANATING DEVICE

(71) Applicant: Firmenich SA, Satigny (CH)

(72) Inventors: Nicholas O'Leary, Plainsboro, NJ (US); Simon Hurry, Southall (GB); Aude Daugeron-Jouault, Neuilly-sur-Seine (FR); James Blumire, Eastleigh (GB)

(73) Assignee: Firmenich SA, Satigny (CH)

( * ) Notice: Subject to any disclaimer, the term of this patent is extended or adjusted under 35 U.S.C. 154(b) by 0 days.

(21) Appl. No.: 15/762,705

(22) PCT Filed: Sep. 30, 2016

(86) PCT No.: PCT/EP2016/073507
§ 371 (c)(1),
(2) Date: Mar. 23, 2018

(87) PCT Pub. No.: WO2017/055603
PCT Pub. Date: Apr. 6, 2017

(65) Prior Publication Data
US 2018/0264156 A1    Sep. 20, 2018

Related U.S. Application Data

(60) Provisional application No. 62/236,799, filed on Oct. 2, 2015, provisional application No. 62/343,995, filed on Jun. 1, 2016.

(30) Foreign Application Priority Data

Jan. 20, 2016  (EP) .................................... 16152076

(51) Int. Cl.
*A61L 9/01* (2006.01)
*A61Q 13/00* (2006.01)
(Continued)

(52) U.S. Cl.
CPC .................................. *A61L 9/01* (2013.01); *A61K 8/04* (2013.01); *A61K 8/411* (2013.01); *A61K 8/42* (2013.01);
(Continued)

(58) Field of Classification Search
CPC .................................. A61L 9/01; A61Q 13/00
See application file for complete search history.

(56) References Cited

U.S. PATENT DOCUMENTS

2011/0200549 A1   8/2011  Granier et al.
2012/0263659 A1*  10/2012  Subkowski ........... D06M 15/03
                                                                424/54

(Continued)

FOREIGN PATENT DOCUMENTS

DE    202012013357 U1 *  7/2016  ............. A61K 8/498
WO    WO2012061698 A2    5/2012
(Continued)

OTHER PUBLICATIONS

English Machine Translation obtained from https://worldwide.espacenet.com/singleLineSearch?locale=en_EP (Year: 2012).*
(Continued)

*Primary Examiner* — Arrie L Reuther
(74) *Attorney, Agent, or Firm* — Armstrong Teasdale LLP

(57) ABSTRACT

The present invention relates to the field of perfumery. It relates more particularly to perfume dispensing device. The device of the present invention comprises dispensing means and a liquid composition including a perfume and selected compounds which impacts the fragrance perception diffused in the surrounding air during use.

8 Claims, 4 Drawing Sheets

(51) Int. Cl.
  *A61L 9/14* (2006.01)
  *A61K 8/49* (2006.01)
  *A61Q 15/00* (2006.01)
  *A61L 9/013* (2006.01)
  *A61K 8/04* (2006.01)
  *A61K 8/42* (2006.01)
  *A61K 8/41* (2006.01)
  *C11B 9/00* (2006.01)

(52) U.S. Cl.
  CPC ............... *A61K 8/49* (2013.01); *A61K 8/494* (2013.01); *A61K 8/4973* (2013.01); *A61K 8/4986* (2013.01); *A61L 9/013* (2013.01); *A61L 9/14* (2013.01); *A61Q 13/00* (2013.01); *A61Q 15/00* (2013.01); *C11B 9/00* (2013.01)

(56) References Cited

U.S. PATENT DOCUMENTS

| | | | |
|---|---|---|---|
| 2014/0017287 A1* | 1/2014 | Lei | A61K 8/84 424/401 |
| 2015/0313820 A1* | 11/2015 | Kulke | A23G 4/06 424/48 |
| 2016/0008297 A1* | 1/2016 | Schmaus | A61K 9/0014 424/48 |

FOREIGN PATENT DOCUMENTS

| | | |
|---|---|---|
| WO | WO2014090293 A1 | 6/2014 |
| WO | WO2014195689 A1 | 12/2014 |

OTHER PUBLICATIONS

International Search Report and Written Opinion, application PCT/EP2016/073507 dated Mar. 15, 2017.

* cited by examiner

FIG. 2

PERFUME EMANATING DEVICE

TECHNICAL FIELD

The present invention relates to the field of perfumery. It relates more particularly to perfume dispensing device. The device of the present invention comprises a liquid composition including a perfume and a perfume modulating compound which impacts the fragrance perception diffused in the surrounding air during use.

BACKGROUND

The use of devices for delivering within the domestic environment via a variety of mechanisms liquids, and commonly volatile liquids, containing one or more active materials wherein the active material comprises at least one of: a fragrance; an insecticide; a fungicide; a pesticide; a sanitising material; and/or a pharmaceutical has become more and more current in recent years. Air-freshening devices or deodorizers are currently used in practically all households to mask bad odors or to diffuse fragrances or other volatile active ingredients to the air surrounding the device, in particular in rooms and cupboards, litter containers, and other closed environments. Emanating devices are also used in other areas of perfumery, like traditionally for fine fragrances, and also for personal care products such as deodorant or antiperspirant.

Amongst the various types of devices that can be used to emanate fragrances and other air modifying substances such as purifying or sanitizing agents, one class of systems is aerosol canister wherein the canister holds the liquid under pressure and when a valve is opened the liquid is forced out. The liquid is provided with a propellant which evaporates inside the canister to maintain an even pressure and, outside the canister, assist with the mechanical break-up of the liquid by evaporating rapidly. Suitable propellants include volatile hydrocarbons such as propane, butane or isobutane. Aerosols generally provide a satisfactory spray performance but since they require manual operation by a user, they are not considered to be particularly convenient for routine use. Automatic aerosol activation devices exist for operation with metered dose aerosols containing a single phase liquid and propellant mixture. These devices are operable to periodically actuate the aerosol to cause a dose of the liquid to be sprayed. All of the known emanation devices and methodologies of emanation possess advantages and disadvantages with respect to each other that will be appreciated by a person skilled in the art as well as the ultimate end user.

In terms perfume emanation when using such devices, the consumer is sensible to the overall fragrance experience and in this regard, the perfume industry is constantly looking at ways of enhancing the perception of the perfume, such its diffusion in the air, its lasting overtime, limiting perfume habituation etc. WO2014195689 has for instance recently described new compositions designed to prevent habituation to a fragrance used in particular in air freshening composition, therefore improving the consumer experience when using such devices.

It is therefore always desirable to add extra benefit to the overall experience of the consumer when using in particular an air freshener. Improving the diffusion of a perfume when using an emanating device in application when at least part of the fragrance is diffused in the air as is the case for instance in the case of perfumes, eau de cologne, eau de parfum, eaux de toilettes, body sprays, body splashes, or personal deodorants is also something that the industry is always looking for.

The invention provides a novel solution that answers those needs with a composition suitable for being delivered at least partly in the air via an emanating device, said composition comprising selected compounds which are positively modulating the overall experience for the consumer of the fragrance dispensed in the air. Some of those particular compounds used are described in WO2012061698. This application describes those compounds as modulators of transient receptor potential channel melastin member 8 (TRPM8), a channel involved in particular with cooling sensation, and products containing those compounds, wherein there is a surface contact such as skin or mucosa contact with the person or animal during use. However, there is no teaching or suggestion regarding the fact that those ingredients could impact a fragrance perception in the airborne.

DESCRIPTION OF FIGURES

FIG. 2 shows the results of a test aerosol with a compound of the invention and without a compound of the invention.

DESCRIPTION OF THE INVENTION

Figure 1:
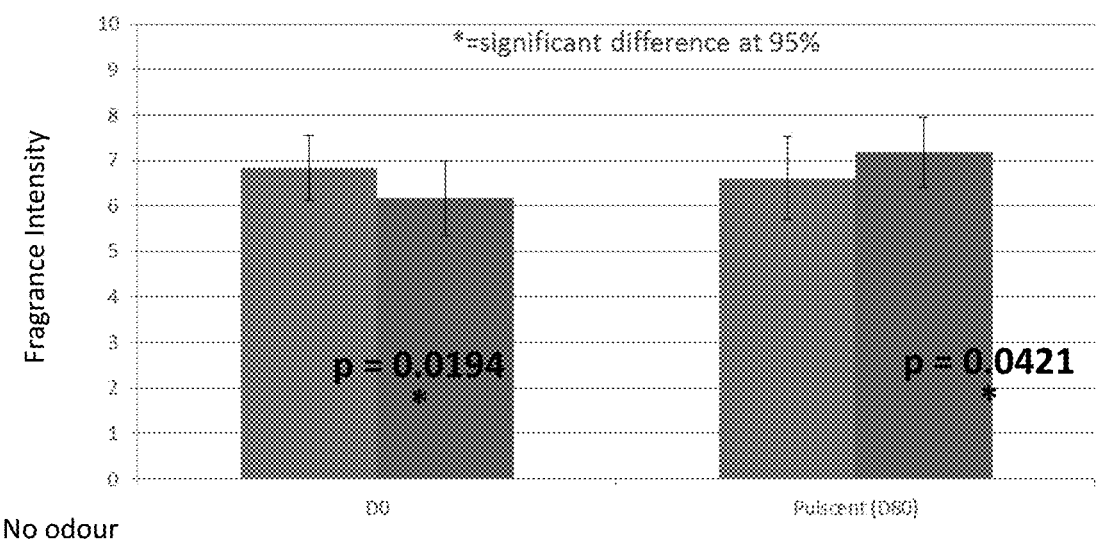
FIG. 1 represents the results of a blind test evaluation, after about 30 minutes at 32° C., of a composition according to this invention against the blank at distance zero and distance 80 cm.

Unless otherwise specified, percentages are meant to designate percentages by weight.

The present invention relates to a device suitable for delivering a liquid composition at least partly in the air and including as part of such liquid composition a perfume and at least one selected compound. It has been found that surprisingly the presence of the latter compound in the composition to be dispensed was positively modulating the overall perfume sensorial experience in the airborne. By modulating the overall sensorial experience of a perfume, it is meant that consumers are noticing a positive effect on the fragrance perception without any alteration or modification of the odor profile itself. Also, the technical effect provided by the presence of the selected compounds in the perfume when delivered at least partly in the air is not limited to just one perceived sensation which is why it is referred to as a modulating effect, but include two or three types of perceived sensations.

Therefore, a first object of the invention consists of a device comprising a liquid composition to be dispensed at least partly in the air, wherein said composition comprises a perfume and an effective amount of at least one compound ("Formula Compound") selected from the group consisting of:

a) an N-substituted-p-menthane-3-carboxamide;
b) an acyclic carboxamide;

c) a compound according to Formula I or II below wherein a compound of Formula I is represented by:

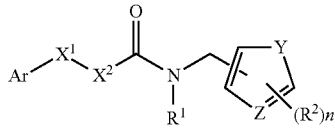

wherein
Ar is optionally substitute aryl, optionally substituted carbocyclyl, or optionally substituted heteroaryl;
Y is oxygen or sulfur;
Z is nitrogen or CR;
R is hydrogen or lower alkyl;
$X^1$-$X^2$ is O—$CR^{2a}R^{2b}$ or $CR^3$=$CR^4$;
$R^{2a}$, $R^{2b}$, $R^3$, and $R^4$ are independently hydrogen or lower alkyl;
$R^1$ is a hydrogen, an optionally substituted alkyl or an optionally substituted five membered heteroaryl;
n is 0, 1, 2 or 3 and
each $R^2$ is independently optionally substituted alkyl, optionally substituted heteroalkyl, optionally substituted alkenyl, alkoxy, hydroxyl, amino, N-alkyl amino, N-diakyl amino, halo, nitro, cyano, acyl, carboxyl, carboxyl ester, or amide,
wherein each optional substituent is selected from the group consisting of alkyl, heteoralkyl, alkenyl, alkoxy, hydroxyl, amino, N-akyl amino, N-diakyl amino, halo, nitro, cyano, acyl, carboxyl, carboxyl ester, or amide; or two substituents, together with the atoms to which they are attached, form a carbocyclyl optionally substituted with alkyl or alkoxy; or two substituents, together with the atoms to which they are attached, form a heterocyclyl containing one or more heeroatom(s) selected from nitrogen, oxygen, and sulphur and a compound of Formula II is represented by:

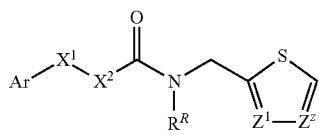

wherein
Ar is optionally substituted aryl, optionally substituted carbocyclyl, or optionally substituted heteroaryl;
$X^1$-$X^2$ is O—$CR^{2a}R^{2b}$, $CR^3$—$CR^4$, $CHR^5$—$CHR^6$, or cycloalkyl;
$R^{2a}$, $R^{2b}$, $R^3$, $R^4$, $R^5$, and $R^6$ are independently hydrogen or lower alkyl;
$Z^1$ and $Z^2$ are independently nitrogen or CH, provided that $Z^1$ and $Z^2$ are not both nitrogen; and
$R^1$ is an optionally substituted five-membered heteroaryl, hydrogen or a optionally substituted akyl;
wherein each optional substituent is selected from the group consisting of alkyl, heteroalkyl, alkenyl, alkoxy, hydroxyl, amino, N-alkyl amino, N-dialkyl amino, halo, nitro, cyano, acyl, carboxyl, carboxyl ester, or amide; or two substituents together with the atoms to which they are attached, form a carbocyclyl optionally substituted with alkyl or alkoxy; or two substituents, together with the atoms to which they are attached, from a heterocyclyl containing one or more heteroatom(s) selected from nitrogen, oxygen, and sulphur;

d) a compound selected from the group consisting of:
3,4-methylenedioxycinnamic acid, N,N-diphenylamide;
N-(1H-pyrazol-5-yl)-N-(thiophen-2-ylmethyl)-2-(p-tolyloxy)acetamide;
N-ethyl-N-(thiophen-2-ylmethyl)-2-(p-tolyloxy)acetamide;
2-(2,3-dihydro-1H-inden-5-yloxy)-N-(1H-pyrazol-3-yl)-N-(thiophen-2-ylmethyl)acetamide;
2-(2,3-dihydro-1H-inden-5-yloxy)-N-(1H-pyrazol-5-yl)-N-(thiophen-2-ylmethyl)acetamide;
2-(2,3-dihydro-1H-inden-5-yloxy)-N-(4-methyl-1H-pyrazol-3-yl)-N-(thiophen-2-ylmethyl)acetamide;
2-(2,3-dihydro-1H-inden-5-yloxy)-N-(1H-pyrazol-4-yl)-N-(thiophen-2-ylmethyl)acetamide;
N-(oxazol-2-yl)-N-(thiophen-2-ylmethyl)-2-(p-tolyloxy)acetamide;
2-(2,3-dihydro-1H-inden-5-yloxy)-N-(3,5-dimethyl-1H-pyrazol-4-yl)-N-(thiophen-2-ylmethyl)acetamide;
N-(3,5-dimethyl-1H-pyrazol-4-yl)-N-(thiophen-2-ylmethyl)-2-(p-tolyloxy)acetamide;
N-(3-methyl-1H-pyrazol-4-yl)-N-(thiophen-2-ylmethyl)-2-(p-tolyloxy)acetamide;
2-(benzo[d][1,3]dioxol-5-yloxy)-N-(1H-pyrazol-5-yl)-N-(thiophen-2-ylmethyl)acetamide;
2-(benzo[d][1,3]dioxol-5-yloxy)-N-(3,5-dimethyl-1H-pyrazol-4-yl)-N-(thiophen-2-ylmethyl)acetamide;
4-(N-(thiophen-2-ylmethyl)-2-(p-tolyloxy)acetamido)-1H-pyrazol-2-ium chloride;
N-(1H-pyrazol-4-yl)-N-(thiophen-2-ylmethyl)-2-(p-tolyloxy)acetamide;
N-(isoxazol-3-yl)-N-(thiophen-2-ylmethyl)-2-(p-tolyloxy)acetamide;
N-(1-(cyanomethyl)-1H-pyrazol-3-yl)-N-(thiophen-2-ylmethyl)-2-(p-tolyloxy)acetamide;
2-(benzo[d][1,3]dioxol-5-yloxy)-N-(3-methyl-1H-pyrazol-4-yl)-N-(thiophen-2-ylmethyl)acetamide;
2-(benzo[d][1,3]dioxol-5-yloxy)-N-(1H-pyrazol-4-yl)-N-(thiophen-2-ylmethyl)acetamide;
N-cyclopropyl-N-(thiophen-2-ylmethyl)-2-(p-tolyloxy)acetamide;
N-allyl-N-(thiophen-2-ylmethyl)-2-(p-tolyloxy)acetamide;
N-(1H-pyrazol-4-yl)-N-(thiophen-2-ylmethyl)-3-p-tolylpropanamide;
2-(4-methoxyphenoxy)-N-(1H-pyrazol-4-yl)-N-(thiophen-2-ylmethyl)acetamide;
N-propyl-N-(thiophen-2-ylmethyl)-2-(p-tolyloxy)acetamide;
N-allyl-2-(benzo[d][1,3]dioxol-5-yloxy)-N-(thiophen-2-ylmethyl)acetamide;
2-(2,3-dihydro-1H-inden-5-yloxy)-N-(pyridin-3-yl)-N-(thiophen-2-ylmethyl)acetamide;
2-(3-methoxyphenoxy)-N-(1H-pyrazol-4-yl)-N-(thiophen-2-ylmethyl)acetamide;
N-(pyridin-4-yl)-N-(thiophen-2-ylmethyl)-2-(p-tolyloxy)acetamide;
N-isopropyl-N-(thiophen-2-ylmethyl)-2-(p-tolyloxy)acetamide;
N-(bicyclo [2.2.1] heptan-2-ylmethyl)-N-(1H-pyrazol-3-yl)-2-(p-tolyloxy)acetamide;
N-ethyl-N-(thiophen-3-ylmethyl)-2-(p-tolyloxy)acetamide;
2-phenoxy-N-phenyl-N-(thiophen-2-ylmethyl)acetamide;
2-(2,3-dihydro-1H-inden-5-yloxy)-N-phenyl-N-(thiophen-2-ylmethyl) acetamide;
N-(bicyclo [2.2.1] heptan-2-ylmethyl)-3-phenyl-N-(1H-pyrazol-3-yl) propanamide;
N-(pyridin-3-yl)-N-(thiophen-2-ylmethyl)-2-(p-tolyloxy) acetamide;

N-ethyl-N-((5-methylthiophen-2-yl)methyl)-2-(p-tolyloxy) acetamide; Example 54.
N 2-(4-ethylphenoxy)-N-(pyridin-3-yl)-N-(thiophen-2-ylmethyl)acetamide;
N-(1-methyl-1H-pyrazol-5-yl)-N-(thiophen-2-ylmethyl)-2-(p-tolyloxy)acetamide;
N-(bicyclo[2.2.1]heptan-2-ylmethyl)-2-phenoxy-N-(1H-pyrazol-3-yl)acetamide;
2-(benzo[d][1,3]dioxol-5-yloxy)-N-(pyridin-3-yl)-N-(thiophen-2-ylmethyl)acetamide;
N-ethyl-2-(4-fluorophenoxy)-N-(thiophen-2-ylmethyl)acetamide;
N-sec-butyl-N-(thiophen-2-ylmethyl)-2-(p-tolyloxy)acetamide;
2-(4-chlorophenoxy)-N-phenyl-N-(thiophen-2-ylmethyl)acetamide;
N-phenyl-N-(thiazol-2-ylmethyl)-2-(p-tolyloxy)acetamide;
N-methyl-N-(thiophen-2-ylmethyl)-2-(p-tolyloxy)acetamide;
3-(2-(3-methoxyphenoxy)-N-(thiophen-2-ylmethyl)acetamido)pyridinium chloride;
2-(3-methoxyphenoxy)-N-(pyridin-2-yl)-N-(thiophen-2-ylmethyl)acetamide;
2-(2-isopropyl-5-methylphenoxy)-N-(1H-pyrazol-3-yl)-N-(thiophen-2-ylmethyl)acetamide;
N-((5-methylthiophen-2-yl)methyl)-N-phenyl-2-(p-tolyloxy)acetamide;
N-(pyridin-2-yl)-N-(thiophen-2-ylmethyl)-2-(m-tolyloxy)acetamide;
N-(pyridin-3-yl)-N-(thiophen-2-ylmethyl)-2-(m-tolyloxy)acetamide;
2-(3,4-dimethylphenoxy)-N-(pyridin-2-yl)-N-(thiophen-2-ylmethyl)acetamide;
2-(4-ethylphenoxy)-N-(pyridin-2-yl)-N-(thiophen-2-ylmethyl)acetamide;
2-(3-methoxyphenoxy)-N-(pyridin-3-yl)-N-(thiophen-2-ylmethyl)acetamide;
N-ethyl-3-phenyl-N-(thiophen-2-ylmethyl)propanamide;
N-ethyl-N-(thiazol-5-ylmethyl)-2-(p-tolyloxy)acetamide;
(R)—N-(3-methylbutan-2-yl)-2-(3-nitrophenoxy)acetamide;
N-ethyl-2-phenoxy-N-(thiophen-2-ylmethyl)acetamide;
((R)—N-(1-hydroxy-3-methylbutan-2-yl)-N-isopropyl-2-(m-tolyloxy)acetamide;
N-(4-fluorophenyl)-N-(thiophen-2-ylmethyl)-2-(p-tolyloxy) acetamide;
2 3,4,6-trimethyl-N-(pyridin-2-yl)-N-(thiophen-2-ylmethyl) benzofuran-2-car boxamide;
2-(4-methoxyphenoxy)-N-(pyridin-3-yl)-N-(thiophen-2-ylmethyl)acetamide;
3,5-dimethyl-N-(pyridin-2-yl)-N-(thiophen-2-ylmethyl) benzofuran-2-carboxamide;
2-(3-methoxyphenoxy)-N-(pyridin-2-yl)-N-(thiophen-2-ylmethyl)acetamide;
N-allyl-2-(2-hydroxyphenoxy)-N-((5-methylthiophen-2-yl) methyl)acetamide;
N-(pyrazin-2-yl)-N-(thiophen-2-ylmethyl)-2-(p-tolyloxy) acetamide;
2-(4-isopropylphenoxy)-N-(pyridin-2-yl)-N-(thiophen-2-ylmethyl)acetamide;
2-(4-fluorophenoxy)-N-(pyridin-3-yl)-N-(thiophen-2-ylmethyl)acetamide;
N-benzyl-N-ethyl-2-(p-tolyloxy)acetamide;
2-(4-chlorophenoxy)-N-(pyridin-2-yl)-N-(thiophen-2-ylmethyl)acetamide;
2-(4-bromophenoxy)-N-(pyridin-2-yl)-N-(thiophen-2-ylmethyl)acetamide;
N-(2-chlorophenyl)-N-(thiophen-2-ylmethyl)-2-(p-tolyloxy)acetamide;
2-(2-isopropyl-5-methylcyclohexyloxy)-N-(2-(pyridin-4-yl) ethyl)acetamide;
N-(thiazol-2-yl)-N-(thiophen-2-ylmethyl)-2-(p-tolyloxy)acetamide;
N-(cyclohexylmethyl)-2-(2,4-dimethylphenoxy)-N-(pyridin-2-yl)acetamide;
N-(furan-2-ylmethyl)-N-(pyridin-2-yl)-2-(p-tolyloxy)acetamide;
3,6-dimethyl-N-(pyridin-2-yl)-N-(thiophen-2-ylmethyl) benzofuran-2-carboxamide;
2-(3-fluorophenoxy)-N-(pyridin-3-yl)-N-(thiophen-2-ylmethyl)acetamide;
N-ethyl-N-(thiazol-2-ylmethyl)-2-(p-tolyloxy)acetamide;
N-ethyl-N-(3-fluorobenzyl)-2-(p-tolyloxy)acetamide;
3,5,6-trimethyl-N-(pyridin-2-yl)-N-(thiophen-2-ylmethyl) benzofuran-2-carboxamide;
N-((5-ethylthiophen-2-yl)methyl)-N-phenyl-2-(p-tolyloxy) acetamide;
N-((5-ethylthiophen-2-yl)methyl)-N-phenyl-2-(p-tolyloxy) acetamide;
N-(pyrimidin-2-yl)-N-(thiophen-2-ylmethyl)-2-(p-tolyloxy) acetamide;
2-phenoxy-N-(pyridin-3-yl)-N-(thiophen-2-ylmethyl)acetamide;
2-(4-fluorophenoxy)-N-(pyridin-2-yl)-N-(thiophen-2-ylmethyl)acetamide;
N-(thiophen-2-ylmethyl)butan-1-amine;
2-(3-chlorophenoxy)-N-(pyridin-2-yl)-N-(thiophen-2-ylmethyl)acetamide;
N-((3-methylthiophen-2-yl)methyl)-N-phenyl-2-(p-tolyloxy)acetamide:
2-phenoxy-N-(pyridin-2-yl)-N-(thiophen-2-ylmethyl)acetamide:
(E)-3-(benzo[d][1,3]dioxol-5-yl)-N-(1H-pyrazol-5-yl)-N-(thiophen-2-ylmethyl)acrylamide;
(E)-N-(5-methyl-1H-pyrazol-4-yl)-N-(thiophen-2-ylmethyl)-3-p-tolylacrylamide;
(E)-N-(1H-pyrazol-5-yl)-N-(thiophen-2-ylmethyl)-3-p-tolylacrylamide;
(E)-N-(1H-pyrazol-4-yl)-N-(thiophen-2-ylmethyl)-3-p-tolylacrylamide;
(E)-3-p-tolylacryloyl chloride.
N-(thiophen-2-ylmethyl)-1H-pyrazol-4-amine.
E)-3-(benzo[d][1,3]dioxol-5-yl)-N-(1H-pyrazol-4-yl)-N-(thiophen-2-ylmethyl)acrylamide
(E)-N-(3,5-dimethyl-1H-pyrazol-4-yl)-N-(thiophen-2-ylmethyl)-3-p-tolylacrylamide;
(E)-3-(benzo [d][1,3]dioxol-5-yl)-N-(5-methyl-1H-pyrazol-4-yl)-N-(thiophen-2-ylmethyl)acrylamide;
(E)-3-(benzo [d][1,3]dioxol-5-yl)-N-cyclopropyl-N-(thiophen-2-ylmethyl)acrylamide;
E)-3-(benzo[d][1,3]dioxol-5-yl)-N-ethyl-N-(thiophen-2-ylmethyl)acrylamide;
(E)-3-(benzo [d][1,3]dioxol-5-yl)-N-(3,5-dimethyl-1H-pyrazol-4-yl)-N-(thiophen-2-ylmethyl)acrylamide;
(E)-N-ethyl-N-(thiophen-2-ylmethyl)-3-p-tolylacrylamide;
(E)-3-(4-methoxyphenyl)-N-(1H-pyrazol-4-yl)-N-(thiophen-2-ylmethyl)acrylamide;
(E)-3-(4-methoxyphenyl)-N-(1H-pyrazol-5-yl)-N-(thiophen-2-ylmethyl)acrylamide;
N-(1H-pyrazol-5-yl)-N-(thiophen-2-ylmethyl)-3-p-tolylpropanamide;
N-(3,5-dimethyl-1H-pyrazol-4-yl)-N-(thiophen-2-ylmethyl) cinnamamide;

N-(1H-pyrazol-5-yl)-N-(thiophen-2-ylmethyl)cinnamamide;
N-(1H-pyrazol-4-yl)-N-(thiophen-2-ylmethyl)cinnamamide;
(E)-3-(2,3-dihydro-1H-inden-5-yl)-N-(3,5-dimethyl-1H-pyrazol-4-yl)-N(thiophen-2-ylmethyl) acrylamide;
((E)-3-(benzo[d][1,3]dioxol-5-yl)-N-(pyridin-3-yl)-N-(thiophen-2-ylmethyl)acrylamide;
(+/−) (E)-2-phenyl-N-(1H-pyrazol-4-yl)-N-(thiophen-2-ylmethyl)cyclopropanecarboxamide
(E)-3-(benzo[d][1,3]dioxol-5-yl)-N-(pyridin-2-yl)-N-(thiophen-2-ylmethyl)acrylamide;
2-phenoxy-N-(1H-pyrazol-5-yl)-N-(thiophen-2-ylmethyl)acetamide;
(E)-3-(2,3-dihydro-1H-inden-5-yl)-N-(1H-pyrazol-5-yl)-N-(thiophen-2-ylmethyl) Acrylamide
(E)-3-(2,3-dihydro-1H-inden-5-yl)-N-(5-methyl-1H-pyrazol-4-yl)-N-(thiophen-2-ylmethyl) acrylamide;
N-(bicyclo [2.2.1] heptan-2-yl)-N-(1H-pyrazol-5-yl)cinnamamide;
N-ethyl-N-(thiophen-2-ylmethyl)cinnamamide;
2-(2,3-dihydro-1H-inden-5-yloxy)-N-ethyl-N-(thiazol-5-ylmethyl)acetamide;
2-(2,3-dihydro-1H-inden-5-yloxy)-N-ethyl-N-(thiazol-5-ylmethyl)acetamide;
2-(benzo[d][1,3]dioxol-5-yloxy)-N-phenyl-N-(thiophen-2-ylmethyl)acetamide;
N-allyl-N-(thiophen-2-ylmethyl)cinnamamide;
(+/−) (E)-N-ethyl-2-phenyl-N-(thiophen-2-ylmethyl)cyclopropanecarboxamide;
(E)-N-(bicyclo [2.2.1] heptan-2-yl)-N-(1H-pyrazol-5-yl)-3-p-tolylacrylamide;
N-(bicyclo [2.2.1] heptan-2-yl)-2-(2,3-dihydro-1H-inden-5-yloxy)-N-(1H-pyrazol-5-yl) acetamide;
N-(bicyclo [2.2.1]hept-5-en-2-ylmethyl)-N-(1H-pyrazol-5-yl)-2-(p-tolyloxy)acetamide;
2-(cyclohexyloxy)-N-(1H-pyrazol-5-yl)-N-(thiophen-2-ylmethyl)acetamide;
N-(bicyclo [2.2.1] heptan-2-yl)-2-(cyclohexyloxy)-N-(1H-pyrazol-5-yl)acetamide;
3,4,6-trimethyl-N-(pyridin-2-yl)-N-(thiophen-2-ylmethyl)benzofuran-2-carboxamide;
2-(2,3-dihydro-1H-inden-5-yloxy)-N-ethyl-N-((5-methyl-thiophen-2-yl)methyl)acetamide;
(E)-N-phenyl-N-(thiophen-2-ylmethyl)-3-p-tolylacrylamide;
N-phenyl-N-(thiophen-2-ylmethyl)cinnamamide;
N-(pyridin-2-yl)-N-(thiophen-2-ylmethyl)cinnamamide;
(+/−) (E)-N,2-diphenyl-N-(thiophen-2-ylmethyl)cyclopropanecarboxamide;
3,5-dimethyl-N-(pyridin-2-yl)-N-(thiophen-2-ylmethyl)benzofuran-2-carboxamide;
N-(bicyclo [2.2.1] heptan-2-yl)-N-(1H-pyrazol-5-yl)-3-p-tolylpropanamide;
(E)-N-allyl-3-(7-chloro benzo [d][1,3]dioxol-5-yl)-N-(thiophen-2-ylmethyl)acrylamide;
N-(pyridin-3-yl)-N-(thiophen-2-ylmethyl)cinnamamide;
3,6-dimethyl-N-(pyridin-2-yl)-N-(thiophen-2-ylmethyl)benzofuran-2-carboxamide;
(E)-3-(benzo [d][1,3]dioxol-5-yl)-N,N-bis(thiophen-2-ylmethyl)acrylamide;
2-(benzo[d][1,3]dioxol-5-yloxy)-N-phenyl-N-(thiophen-2-ylmethyl)acetamide;
2-(2,3-dihydro-1H-inden-5-yloxy)-N-ethyl-N-(thiophen-2-ylmethyl)acetamide;
2-(2-hydroxy-4-methylphenoxy)-N-(1H-pyrazol-5-yl)-N-(thiophen-2-ylmethyl)acetamide;
N-ethyl-2-(2-hydroxy-4-methylphenoxy)-N-(thiophen-2-ylmethyl)acetamide;
N-phenyl-N-(thiophen-2-ylmethyl)-2-(p-tolyloxy)acetamide;
2-(2,3-dihydrobenzo[b][1,4]dioxin-6-yloxy)-N-phenyl-N-(thiophen-2-ylmethyl)acetamide;
2-(3-methoxyphenoxy)-N-phenyl-N-(thiophen-2-ylmethyl)acetamide;
2-(4-methoxyphenoxy)-N-phenyl-N-(thiophen-2-ylmethyl)acetamide;
2-(4-fluorophenoxy)-N-phenyl-N-(thiophen-2-ylmethyl)acetamide;
2-(benzo[d][1,3]dioxol-5-yloxy)-N-ethyl-N-(thiophen-2-ylmethyl)acetamide;
N-ethyl-2-(3-methoxyphenoxy)-N-(thiophen-2-ylmethyl)acetamide;
N-phenyl-N-(thiophen-2-ylmethyl)-2-(m-tolyloxy)acetamide;
N-ethyl-N-(furan-3-ylmethyl)-2-(p-tolyloxy)acetamide;
N-ethyl-2-(4-methoxyphenoxy)-N-(thiophen-2-ylmethyl)acetamide;
N-ethyl-N-(thiophen-2-ylmethyl)-2-(o-tolyloxy)acetamide;
2-(3-fluorophenoxy)-N-phenyl-N-(thiophen-2-ylmethyl)acetamide;
2-(benzo [d][1,3]dioxol-5-yloxy)-N-ethyl-N-(furan-3-ylmethyl)acetamide;
N-ethyl-3-(4-methoxyphenyl)-N-(thiophen-2-ylmethyl)propanamide;
N-ethyl-N-(thiophen-2-ylmethyl)-2-(m-tolyloxy)acetamide;
N-(pyridin-2-yl)-N-(thiophen-2-ylmethyl)-2-(p-tolyloxy)acetamide;
N-ethyl-2-(2-hydroxyphenoxy)-N-(thiophen-2-ylmethyl)acetamide;
2-(4-ethylphenoxy)-N-phenyl-N-(thiophen-2-ylmethyl)acetamide;
2-(3,4-dimethylphenoxy)-N-phenyl-N-(thiophen-2-ylmethyl)acetamide;
2-(benzo[d][1,3]dioxol-5-yloxy)-N-(pyridin-2-yl)-N-(thiophen-2-ylmethyl)acetamide;
2-(3-chlorophenoxy)-N-phenyl-N-(thiophen-2-ylmethyl)acetamide;
N-ethyl-3-(4-fluorophenyl)-N-(thiophen-2-ylmethyl)propanamide;
2-(2-hydroxyphenoxy)-N-phenyl-N-(thiophen-2-ylmethyl)acetamide;
N-(pyridin-2-yl)-N-(thiophen-2-ylmethyl)-2-(p-tolyloxy)acetamide;
N-ethyl-N-(furan-2-ylmethyl)-2-(p-tolyloxy)acetamide;
N-ethyl-N-(thiophen-2-ylmethyl)-3-o-tolylpropanamide;
2-(2-fluorophenoxy)-N-phenyl-N-(thiophen-2-ylmethyl)acetamide;
N-phenyl-N-(thiophen-2-ylmethyl)-2-(o-tolyloxy)acetamide;
N-ethyl-2-(3-fluorophenoxy)-N-(thiophen-2-ylmethyl)acetamide;
2-(benzo[d][1,3]dioxol-5-yloxy)-N-ethyl-N-(furan-2-ylmethyl)acetamide;
2-(2-chlorophenoxy)-N-phenyl-N-(thiophen-2-ylmethyl)acetamide;
2-(4-isopropylphenoxy)-N-phenyl-N-(thiophen-2-ylmethyl)acetamide;
N-benzyl-N-phenyl-2-(p-tolyloxy)acetamide;
N-ethyl-3-(3-fluorophenyl)-N-(thiophen-2-ylmethyl)propanamide;
N-(pyridin-2-yl)-N-(thiophen-2-ylmethyl)-2-(p-tolyloxy)propanamide;

N-ethyl-N-(thiophen-2-ylmethyl)-2-(p-tolyloxy)propanamide;
N-benzyl-N-phenyl-2-(p-tolyloxy)acetamide;
N-ethyl-3-(3-fluorophenyl)-N-(thiophen-2-ylmethyl)propanamide;
N-ethyl-N-(thiophen-2-ylmethyl)-3-m-tolylpropanamide;
N-phenyl-N-(thiophen-2-ylmethyl)benzofuran-2-carboxamide;
N-ethyl-N-(thiophen-2-ylmethyl)benzofuran-2-carboxamide;
2-(4-cyanophenoxy)-N-ethyl-N-(thiophen-2-ylmethyl)acetamide;
N-(1-methyl-1H-imidazol-2-yl)-N-(thiophen-2-ylmethyl)-2-(p-tolyloxy)acetamide;
N-ethyl-3-(4-methoxyphenyl)-N-(thiophen-2-ylmethyl)propanamide;
N-ethyl-2-(2-fluorophenoxy)-N-(thiophen-2-ylmethyl)acetamide;
2-(4-(hydroxymethyl)phenoxy)-N-phenyl-N-(thiophen-2-ylmethyl)acetamide;
N-cyclohexyl-N-phenyl-2-(p-tolyloxy)acetamide;
2-(6-methyl-4-oxo-4H-chromen-2-yloxy)-N-phenyl-N-(thiophen-2-ylmethyl)acetamide;
N-ethyl-3-(4-oxo-3,4-dihydroquinazolin-2-yl)-N-(thiophen-2-ylmethyl)propanamide;
2-(4-hydroxyphenoxy)-N-phenyl-N-(thiophen-2-ylmethyl)acetamide;
2-(4-cyanophenoxy)-N-phenyl-N-(thiophen-2-ylmethyl)acetamide;
N-propyl-N-(thiophen-2-ylmethyl)-2-(p-tolyloxy)acetamide;
N-(pyridin-2-yl)-N-(thiophen-2-ylmethyl)-3-p-tolylpropanamide;
2-(benzyloxy)-N-phenyl-N-(thiophen-2-ylmethyl)acetamide;
N-phenyl-N-(pyridin-4-ylmethyl)-2-(p-tolyloxy)acetamide;
N-ethyl-2-methyl-N-(thiophen-2-ylmethyl)-2-(p-tolyloxy)propanamide;
N-phenyl-N-(pyridin-4-ylmethyl)-2-(p-tolyloxy)acetamide;
N-ethyl-2-methyl-N-(thiophen-2-ylmethyl)-2-(p-tolyloxy)propanamide;
2-(2-hydroxy-4-methylphenoxy)-N-(1H-pyrazol-4-yl)-N-(thiophen-2-ylmethyl)acetamide;
(E)-N-ethyl-3-(4-methoxyphenyl)-N-(thiophen-2-ylmethyl)acrylamide;
(E)-N-ethyl-N-(furan-3-ylmethyl)-3-p-tolylacrylamide;
(E)-N-ethyl-N-(thiophen-2-ylmethyl)-3-o-tolylacrylamide;
(E)-3-(benzo [d][1,3]dioxol-5-yl)-N-ethyl-N-(furan-3-ylmethyl)acrylamide;
(E)-3-(2,3-dihydrobenzofuran-5-yl)-N-ethyl-N-(thiophen-2-ylmethyl)acrylamide
(E)-3-(2,3-dihydrobenzo[b][1,4]dioxin-6-yl)-N-ethyl-N-(thiophen-2-25 ylmethyl)acrylamide;
N-ethyl-S-methyl-N-(thiophen-2-ylmethyl)benzofuran-2-carboxamide;
N-ethyl-N-(thiophen-2-ylmethyl)-3-p-tolylpropanamide;
(E)-N-ethyl-3-(4-fluorophenyl)-N-(thiophen-2-ylmethyl)acrylamide;
(E)-3-(2,3-dihydro-1H-inden-5-yl)-N-ethyl-N-(furan-3-ylmethyl)acrylamide;
(E)-N-ethyl-3-(5-methylthiophen-2-yl)-N-(thiophen-2-ylmethyl)acrylamide;
(E)-3-(benzo [d][1,3]dioxol-5-yl)-N-ethyl-N-(furan-2-ylmethyl)acrylamide;
(E)-3-(2,3-dihydro-1H-inden-5-yl)-N-ethyl-N-(thiophen-2-ylmethyl)acrylamide;
(E)-N-ethyl-3-(3-hydroxy-4-methoxyphenyl)-N-(thiophen-2-ylmethyl)acrylamide;
(E)-N-ethyl-N-(furan-2-ylmethyl)-3-p-tolylacrylamide;
(E)-N-ethyl-3-(2-fluorophenyl)-N-(thiophen-2-ylmethyl) acrylamide;
(E)-N-ethyl-N-(thiophen-2-ylmethyl)-3-m-tolylacrylamide;
(E)-N-ethyl-3-(3-methoxyphenyl)-N-(thiophen-2-ylmethyl)acrylamide;
(E)-3-(2,2-difluorobenzo[d][1,3]dioxol-5-yl)-N-ethyl-N-(thiophen-2-ylmethyl)acrylamide
(E)-N-ethyl-3-(3-fluorophenyl)-N-(thiophen-2-ylmethyl)acrylamide
(E)-N-ethyl-3-(5-methylfuran-2-yl)-N-(thiophen-2-ylmethyl)acrylamide
(E)-3-(4-cyanophenyl)-N-ethyl-N-(thiophen-2-ylmethyl)acrylamide
E)-N-ethyl-3-(thiophen-2-yl)-N-(thiophen-2-ylmethyl)acrylamide;
(E)-3-(2-cyanophenyl)-N-ethyl-N-(thiophen-2-ylmethyl)acrylamide;
(E)-3-(2,3-dihydro-1H-inden-5-yl)-N-ethyl-N-(furan-2-ylmethyl)acrylamide;
3-(2,3-dihydro-1H-inden-5-yl)-N-ethyl-N-(thiophen-2-ylmethyl)propanamide
(E)-N-ethyl-N-(thiophen-2-ylmethyl)-3-(thiophen-3-yl) acrylamide
(E)-3-(3-cyanophenyl)-N-ethyl-N-(thiophen-2-ylmethyl)acrylamide;
(E)-N-ethyl-3-(4-hydroxyphenyl)-N-(thiophen-2-ylmethyl) acrylamide;
(E)-N-ethyl-3-(1-methyl-1H-pyrrol-2-yl)-N-(thiophen-2-ylmethyl)acrylamide
(E)-N-ethyl-3-(1-methyl-1H-pyrrol-2-yl)-N-(thiophen-2-ylmethyl)acrylamide;
(E)-N-ethyl-3-(2-methoxyphenyl)-N-(thiophen-2-ylmethyl) acrylamide;
(E)-N-ethyl-3-(3-hydroxyphenzl)-N-(thiophene-2-ylmethyl)acrylamide
2-(3-cyanophenoxy)-N-phenyl-N-(thiophen-2-ylmethyl)acetamide;
2-bromo-N-phenyl-N-(thiophen-2-ylmethyl)acetamide;
N-ethyl-2-(2-hydroxy-5-methylphenoxy)-N-(thiophen-2-ylmethyl)acetamide;
N-ethyl-2-(3-fluoro-4-methylphenoxy)-N-(thiophen-2-ylmethyl)acetamide;
2-(3-fluoro-4-methylphenoxy)-N-phenyl-N-(thiophen-2-ylmethyl)acetamide;
2-(4-fluoro-3-methylphenoxy)-N-phenyl-N-(thiophen-2-ylmethyl)acetamide;
2-(5-methylpyridin-2-yloxy)-N-phenyl-N-(thiophen-2-ylmethyl)acetamide;
2-(3-fluoro-4-methoxyphenoxy)-N-phenyl-N-(thiophen-2-ylmethyl)acetamide;
2-(6-methylpyridin-2-yloxy)-N-phenyl-N-(thiophen-2-ylmethyl)acetamide;
2-(6-methylpyridin-3-yloxy)-N-phenyl-N-(thiophen-2-ylmethyl)acetamide;
N-phenyl-N-(thiophen-2-ylmethyl)-2-(4-(trifluoromethyl)phenoxy)acetamide;
N-phenyl-N-(thiophen-2-ylmethyl)-2-(thiophen-2-yloxy) acetamide;
2-(4-allyl-2-methoxyphenoxy)-N-phenyl-N-(thiophen-2-ylmethyl)acetamide;
and e) a compound selected from the group consisting of:
WS-23 (2-Isopropyl-N,2,3-trimethylbutyramide), FEMA 3804; WS-3 (N-Ethyl-p-menthane-3-carboxamide), FEMA 3455; WS-5 [Ethyl 3-(p-menthane-3-carboxamido)acetate], FEMA 4309; WS-12 (1R,2S,5R)—N-(4-Methoxyphenyl)-p-menthanecarboxamide, FEMA 4681; WS-27 (N-Ethyl-2,2-diisopropylbutanamide), FEMA 4557; N-Cyclopropyl-5-methyl-2-isopropylcyclohexanecarboxamide, FEMA 4693, WS-116 (N-(1,1-Dimethyl-2-hydroxyethyl)-2,2-diethylbutanamide), FEMA 4603; Menthoxyethanol, FEMA 4154; N-(4-cyanomethylphenyl)-p-menthanecarboxamide, FEMA 4496; N-(2-(Pyridin-2-yl)ethyl)-3-p-menthanecarboxamide, FEMA 4549; N-(2-Hydroxyethyl)-2-isopropyl-2,3-dimethylbutanamide, FEMA 4602 and (also N-(4-(carbamoylmethyl)phenyl)-menthylcarboxamide, FEMA 4684; (1R,2S,5R)—N-(4-Methoxyphenyl)-p-menthanecarboxamide (WS-12), FEMA 4681; (2S,5R)—N-[4-(2-Amino-2-oxoethyl)phenyl]-p-menthanecarboxamide, FEMA 4684; and N-Cyclopropyl-5-methyl-2-isopropylcyclohexanecarbonecarboxamide, FEMA 4693; 2-[(2-p-Menthoxy)ethoxy]ethanol, FEMA 4718, (2,6-Diethyl-5-isopropyl-2-methyltetrahydropyran, FEMA 4680); trans-4-tert-Butylcyclohexanol, FEMA 4724; (-)-Menthol, FEMA 2665; Isopulegol. FEMA 2962; (-)-Menthyl lactate, FEMA 37483; -((-)-Menthoxy)propane-1,2-diol, FEMA 3784; (-)-Menthyl ethylene glycol carbonate, FEMA 3805; (-)-Menthone 1,2-glycerol ketal, FEMA 3807; (racemic)=DL-Menthone 1,2-glycerol ketal, FEMA 3808; (-)-Menthyl succinate, FEMA 3810; (-)-Menthyl 1&2 propylene glycol carbonates, FEMA 3806; (racemic)=DL-Menthyl 1&2 propylene glycol carbonates, FEMA 3992; Menthyl glutarate, FEMA 4006; (+)-cis & (-)-trans p-menthane-3,8-diol, FEMA 4053; Menthyl pyrrolidone carboxylate, FEMA 4155; N,N-Dimethyl (-)-menthyl succinamide, FEMA 4230; (-)-Menthone (S)-lactic acid ketal, FEMA; 4285; (-)-Menthyl (S)-3-hydroxybutyrate, FEMA 4308; (-)-Menthyl acetoacetate FEMA 4327; (1R,2S,5R)—N-(4-(cyanomethyl)phenyl)menthylcarboxamide, FEMA 4496; (-)-Cubebol=(1R,4S,5R,6R,7S,10R)-7-isopropyl-4,10-dimethyl-tricyclo[4.4.0.0(1,5)]decan-4-ol, FEMA 4497; 1R,2S,5R)—N-(2-(pyridin-2-yl)ethyl)menthylcarboxamide, FEMA 4549; N-(2-Hydroxyethyl)-2,3-dimethyl-2-isopropylbutanamide, FEMA 4602; Di-(-)-menthyl glutarate, FEMA 4604; (1R,2S,5R)—N-(4-(carbamoylmethyl)phenyl)-menthylcarboxamide, FEMA 4684; 2-[2-(p-menthan-3-yloxy)ethoxy]ethanol=(1R,2S,5R)-2-[2-(2-Isopropyl-5-methyl-cyclohexyloxy)ethoxy]-ethanol, FEMA 4718; 1R,2R,4R)-1-(2-Hydroxy-4-methylcyclohexyl)ethanone, FEMA 4742; and 2-(p-tolyloxy)-N-(1H-pyrazol-5-yl)-N-((thiophen-2-yl)methyl)acetamide, FEMA 4809.

In one embodiment of Formula I Ar is an optionally substituted phenyl.

In another embodiment of Formula I, Ar is optionally substituted heteroaryl, wherein the heteroaryl is a five- or six-membered heteroaryl containing one or more heteroatoms selected from nitrogen, oxygen and sulfur, more particularly Ar is an optionally substituted group selected from the group consisting of pyrrolyl, furanyl, thienyl, pyrazolyl, triazolyl, oxazolyl, thiazolyl, isoxazolyl, isothiazolyl, pyridyl, pyrimidyl and triazinyl.

In a further embodiment, a compound of Formula I is provided wherein each optional substituent of Formula I is selected from the group consisting of alkyl, alkoxy, hydroxyl, halo, nitro and cyano; or two substituents, together with the atoms to which they are attached, form a heterocyclyl containing one or more heteroatom(s) selected from nitrogen, oxygen, and sulfur.

In one embodiment provided herein is a compound of Formula I wherein $R^{2b}$, $R^3$, and $R^4$ are hydrogen.

In one embodiment provided herein is a compound of Formula I where $R^1$ is methyl, ethyl or propyl. In another embodiment provided herein is a compound of Formula I wherein $R^1$ is an optionally substituted group selected from the group consisting of pyrrolyl, furanyl, thienyl, pyrazolyl, triazolyl, oxazolyl and thiazolyl.

In yet a further embodiment provided herein is a compound of Formula I wherein $X^1$-$X^2$ is O—$CH_2$, O—CH($CH_3$), or O—CH($CH_2CH_3$).

In a further embodiment provided herein is a compound of Formula I wherein $X^1$-$X^2$ is CH—CH.

In one embodiment of Formula II a compound is provided wherein Ar is an optionally substituted aryl and $X^1$-$X^2$ is O—$CR^{2a}$—$R^{2b}$, $CH_2$—$CH_2$, or CH=CH.

In one embodiment, a compound of Formula II is provided wherein the wherein Ar is an optionally substituted phenyl.

In one embodiment a compound of Formula II is provided wherein Ar is optionally substituted heteroaryl $X^1$-$X^2$ is O—$CR^{2a}$—$R^{2b}$, $CH_2$—$CH_2$, or CH=CH.

In one embodiment a compound of formula II is provided wherein $Z^1$ and $Z^2$ are CH.

In one embodiment a compound of Formula II is provided wherein $R^{2a}$ and $R^{2b}$ are hydrogen.

In another embodiment provided herein is a compound of Formula I wherein $R^1$ is an optionally substituted group selected from the group consisting of pyrrolyl, furanyl, thienyl, pyrazolyl, triazolyl, oxazolyl and thiazolyl.

In yet a further embodiment provided herein is a compound of Formula I wherein $X^1$-$X^2$ is O—$CH_2$, O—CH($CH_3$), or O—CH($CH_2CH_3$).

In a further embodiment provided herein is a compound of Formula I wherein $X^1$-$X^2$ is CH—CH.

According to another embodiment, a compound for use herein is an amide selected from N-(1H-pyrazol-5-yl)-N-(thiophen-2-ylmethyl)-2-(p-tolyloxy)acetamide and 2-(2,3-dihydro-1H-inden-5-yloxy)-N-(1H-pyazol-5-yl)-N-(thiopene-2-ylmethyl)acetamide.

In a further embodiment, a compound for use herein is an amide selected from N-(1H-pyrazol-5-yl)-N-(thiophen-2-ylmethyl)-2-(p-tolyloxy)acetamide, 3,4-methylenedioxycinnamic acid, N,N-diphenylamide and a mixture thereof.

In a further embodiment, a compound for use herein is N-(1H-pyrazol-5-yl)-N-(thiophen-2-ylmethyl)-2-(p-tolyloxy)acetamide.

In yet another embodiment, a compound for use herein is 2-(2,3-dihydro-1H-inden-5-yloxy)-N-(1H-pyazol-5-yl)-N-(thiopene-2-ylmethyl)acetamide. In one embodiment, a compound for use herein is selected from the group consisting of WS-23 (2-Isopropyl-N,2,3-trimethylbutyramide), FEMA 3804; WS-3 (N-Ethyl-p-menthane-3-carboxamide), FEMA 3455; WS-5 [Ethyl 3-(p-menthane-3-carboxamido)acetate], FEMA 4309; WS-12 (1R,2S,5R)—N-(4-Methoxyphenyl)-p-menthanecarboxamide, FEMA 4681; WS-27 (N-Ethyl-2,2-diisopropylbutanamide), FEMA 4557; (-)-Menthyl lactate, FEMA 37483; -((-)-Menthoxy)propane-1,2-diol, FEMA 3784; (-)-Menthyl ethylene glycol carbonate, FEMA 3805; (-)-Menthone 1,2-glycerol ketal, FEMA 3807; (racemic)=DL-Menthone 1,2-glycerol ketal, FEMA 3808; (-)-Menthyl succinate, FEMA 3810; (-)-Menthyl 1&2 propylene glycol carbonates, FEMA 3806; (racemic)=DL-Menthyl 1&2 propylene glycol carbonates, FEMA 3992; (1R,2S,5R)—N-(4-(cyanomethyl)phenyl)menthylcarboxamide, FEMA 4496; (-)-Cubebol=(1R,4S,5R,6R,7S,10R)-7-isopropyl-4,10-dimethyl-tricyclo[4.4.0.0(1,5)]decan-4-ol, FEMA 4497; 1R,2S,5R)—N-(2-(pyridin-2-yl)ethyl)menthylcarboxamide, FEMA 4549; N-(2-Hydroxyethyl)-2,3-dimethyl-2-isopropylbutanamide, FEMA 4602; Di-(-)-menthyl glutarate, FEMA 4604; (1R,2S,5R)—N-(4-(carbamoylmethyl)phenyl)-menthylcarboxamide, FEMA 4684; 2-[2-(p-menthan-3-yloxy)ethoxy]ethanol=(1R,2S,5R)-2-[2-(2-Isopropyl-5-methyl-cyclohexyloxy)ethoxy]-ethanol, FEMA 4718; 1R,2R,4R)-1-(2-Hydroxy-4-methylcyclohexyl)ethanone, FEMA 4742; and 2-(p-tolyloxy)-N-(1H-pyrazol-5-yl)-N-((thiophen-2-yl)methyl)acetamide, FEMA 4809.

In one embodiment the compound provided here is WS-3 (N-Ethyl-p-menthane-3-carboxamide).

Another object of the invention is a device comprising:
a liquid composition, and
dispensing means to dispense at least partly in the air the composition,
wherein said liquid composition comprises:
i) a perfume and
ii) an effective amount of at least one formula compound A selected from the group consisting of
a) at least one compound according to Formula (IA)

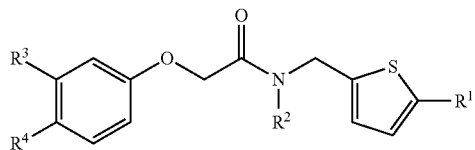

(IA)

wherein $R^1$ represents a hydrogen atom or a methyl group;
$R^2$ represents a pyrazol-5-yl or a pyrazol-4-yl, optionally substituted by one or two methyl groups;
$R^3$, when taken separately, represents a hydrogen atom and $R^4$, when taken separately; represents hydrogen atom or a methyl or methoxy group; or $R^3$ and $R^4$, when taken together, represent a $(CH_2)_3$ or $(OCH_2O)$ group,
b) 3,4-methylenedioxycinnamic acid, N,N-diphenylamide, and
c) mixtures thereof.

According to a particular embodiment, said $R^1$ represents a hydrogen atom.

According to a particular embodiment, said $R^2$ represents a 1H-pyrazol-3-yl, 1H-pyrazol-5-yl or a 1H-pyrazol-4-yl groups, preferably a 1H-pyrazol-5-yl group.

According to a particular embodiment, said $R^3$, when taken separately, represents a hydrogen atom and $R^4$, when taken separately; represents a methyl group; or $R^3$ and $R^4$, when taken together, represent a $(CH_2)_3$ group.

According to a particular embodiment, said compound (IA) is N-(1H-pyrazol-5-yl)-N-(thiophen-2-ylmethyl)-2-(p-tolyloxy)acetamide or 2-((2,3-dihydro-1H-inden-5-yl)oxy)-N-(1H-pyrazol-3-yl)-N-(thiophen-2-ylmethyl)acetamide.

According to an embodiment, the compound (IA) is N-(1H-pyrazol-5-yl)-N-(thiophen-2-ylmethyl)-2-(p-tolyloxy)acetamide (also referred as 2-(4-methylphenoxy)-N-(1H-pyrazol-5-yl)-N-(2-thienylmethyl)acetamide).

However, it should be understood that N-(1H-pyrazol-5-yl)-N-(thiophen-2-ylmethyl)-2-(p-tolyloxy)acetamide also includes its tautomer N-(1H-pyrazol-3-yl)-N-(thiophen-2-ylmethyl)-2-(p-tolyloxy)acetamide (also referred as 2-(4-methylphenoxy)-N-(1H-pyrazol-3-yl)-N-(2-thienylmethyl) acetamide) well-known by the person skilled in the art.

According to the invention, "dispensing means" should be understood as any means suitable to dispense at least partly in the air a liquid composition.

One may cite as non-limiting examples, simple dispensing means such as an opening, a porous wick or more complex dispensing means such as mechanical systems (pump, pressurized spray system) or electrical systems.

Another object of the invention is a device comprising:
a liquid composition, and
dispensing means to dispense at least partly in the air the composition,
wherein said liquid composition comprises:
i) a perfume and
ii) an effective amount of at least one compound selected from the group consisting of N-Ethyl-p-menthane-3-carboxamide (WS-3); 2-Isopropyl-N,2,3-trimethylbutyramide (WS-23); Ethyl 3-(p-menthane-3-carboxamido)acetate (WS-5); N-(1,1-Dimethyl-2-hydroxyethyl)-2,2-diethylbutanamide (WS-116); N-Ethyl-2,2-diisopropylbutanamide (WS-27); (1R,2S,5R)—N-(4-Methoxyphenyl)-p-menthanecarboxamide (WS-12); Menthoxyethanol (Coolact® 5); N-Cyclopropyl-5-methyl-2-isopropylcyclohexanecarboxamide; (−)-Menthol; (−)-Isopulegol (Coolact® P); (−)-Menthyl lactate (Frescolat® ML); 3-((−)-Menthoxy)propane-1,2-diol (Coolact® 10); (−)-Menthyl ethylene glycol carbonate (Frescolat® MGC); (−)-Menthone 1,2-glycerol ketal (Frescolat® MGA); DL-Menthone 1,2-glycerol ketal (Frescolat® MGA (racemic)); (−)-Menthyl succinate; (−)-Menthyl 1&2 propylene glycol carbonates (Frescolat® MPC); DL-Menthyl 1&2 propylene glycol carbonates (Frescolat® Type MPC (racemic)); (−)-Menthyl glutarate (Cooler 2®); (+)-cis & (−)-trans p-menthane-3,8-diol (Coolact® 38D); N,N-Dimethyl (−)-menthyl succinamide; (−)-Menthone (S)-lactic acid ketal (Freshone®), (−)-Menthyl pyrrolidone carboxylate (Questice®); (−)-Menthyl (S)-3-hydroxybutyrate; (−)-Menthyl acetoacetate (Ultracool® 7); (1R,2S,5R)—N-(4-(cyanomethyl)phenyl)menthylcarboxamide (Evercool™ 180); (1R,4S,5R,6R,7S,10R)-7-isopropyl-4,10-dimethyl-tricyclo[4.4.0.0(1,5)]decan-4-ol; (1R,2S,5R)—N-(2-(pyridin-2-yl)ethyl)menthylcarboxamide (Evercool™ 190); N-(2-Hydroxyethyl)-2,3-dimethyl-2-isopropylbutanamide; Di-(−)-menthyl glutarate; (1R,2S,5R)—N-(4-(carbamoylmethyl)phenyl)-menthylcarboxamide; (1R,2S,5R)-2-[2-(2-Isopropyl-5-methyl-cyclohexyloxy)ethoxy]-ethanol; (1R,2R,4R)-1-(2-Hydroxy-4-methylcyclohexyl)ethanone; 2-(p-tolyloxy)-N-(1H-pyrazol-5-yl)-N-((thiophen-2-yl)methyl)acetamide; N-(4-cyanomethylphenyl)-p-menthanecarboxamide; N-(2-(Pyridin-2-yl)ethyl)-3-p-menthanecarboxamide; N-(2-Hydroxyethyl)-2-isopropyl-2,3-dimethylbutanamide; N-(4-(carbamoylmethyl)phenyl)-menthylcarboxamide and mixtures thereof.

The presence of an effective amount of a selected compound provided herein is surprisingly positively modulating the perfume perception by consumers. The sensorial perception of the perfume is altered and the perfume considered as more unique, true-to-life, multi-layered and multisensorial. On the other hand, the odor profile is not affected by the presence of a compound provided herein. Furthermore, fragrance is also being perceived as having improved fragrance diffusion. What is meant by fragrance diffusion in the context of the invention is the perception of a fragrance at a certain distance from an evaporation source, here 80 cm from the source. Fragrance diffusivity is the fragrance intensity perceived at a certain distance evaluated by panellists.

According to any embodiment, the Formula Compound is preferably present in an amount comprised between 0.0005 and 0.2%, preferably between 0.001 to 0.1%; more preferably between 0.002 and 0.01% % by weight of the liquid composition. The exact amount and nature of the Formula Compound will depend on the intended application. In particular, depending on the intended application a skilled person will choose out of "formula compound" as defined in the present invention those having a certain volatility adapted to a particular application. As an example more volatile compounds of "formula compound" as defined in the present invention shall be preferred for use in a liquid electrical air freshener device. Other less volatile compounds might be more suitable for aerosol type devices. Further details on applications are provided below.

The liquid composition comprises a perfume. Said composition can, together with the perfume, comprise further volatile active ingredients. Suitable active ingredients comprise deodorizing or sanitizing agents, or insect repellents, or yet any other volatile materials capable of imparting perceptible and desirable benefits to the quality of the air into which they are diffused. In particular, it is also advantageous to use volatile ingredients that are capable of neutralizing or masking bad odors, i.e. malodor counteracting ingredients.

As "perfume" one may use any perfuming ingredient or a mixture thereof. A "perfuming ingredient" is meant here as a compound which is of use in the perfumery industry, i.e. a compound which is used as active ingredient in perfuming compositions or in perfumed products in order to impart a hedonic effect into its surroundings. In other words, such an ingredient or mixture, to be considered as being a perfuming one, must be able to impart or modify, preferably in a positive or pleasant way, the odor of a composition or product, and not just as having an odor. Moreover, this definition is also meant to include compounds that do not necessarily have an odor but are capable of modulating the odor of a perfuming composition or of a perfumed product and, as a result, of modifying the perception by a user of the odor of such a composition or product.

The nature and type of these perfuming ingredients do not warrant a more detailed description here, which in any case would not be exhaustive, the skilled person being able to select them on the basis of his general knowledge, the intended use or application and the desired organoleptic effect. In general terms, these perfuming ingredients belong to chemical classes as varied as alcohols, aldehydes, ketones, esters, ethers, acetates, nitriles, terpene hydrocarbons, nitrogenous or sulphurous heterocyclic compounds and essential oils. Said perfuming ingredients can be of natural or synthetic origin. Many of these ingredients are in any case listed in reference texts such as the book by S. Arctander, Perfume and Flavor Chemicals, 1969, Montclair, N.J., USA, or its more recent versions, or in other works of a similar nature, as well as in the abundant patent literature in the field of perfumery. It is also understood that said ingredients may also be compounds known to release in a controlled manner various types of perfuming compounds.

Typically, the perfume may also contain a carrier of current use in perfumery such as a solvent. Perfume ingredients or mixtures of ingredients may also be carried in an encapsulated form, enclosed in encapsulating carriers of current use in perfumery. Fragrance microcapsules may be advantageous to protect particularly fragile perfuming ingredients, or yet to delay the release of certain perfume components and thus create a slow release impact. The same applies when so-called pro-fragrances (i.e. chemical substances of high molecular weight, generally not odorant as such but able to generate an odorant by chemical or photochemical reaction under use conditions) are used according to the invention.

The amount of perfume in the liquid composition will depend on the application. A skilled person in the art is able to choose the amount of perfume based on its general knowledge in the application area.

The other active volatile ingredients can be dissolved in any suitable solvent.

By the term "malodor counteractant" or "malodor counteracting ingredient" what is meant here is compounds which are capable of reducing the perception of malodor, i.e. of an odor that is unpleasant or offensive to the human nose, by counteracting and/or masking malodors. In particular embodiments, these compounds have the ability to react with key compounds which are known or suspected to be the cause of the malodor. The reactions result in reduction of the malodor materials' airborne levels and consequent reduction in the perception of the malodor.

The liquid composition can include as further active volatile ingredient an insect repellent. Non-limiting examples of suitable insect repellents include citronella, dimethyl phthalate and n,n-dimethyl-m-tolumide, but any other insect repellent agent can be used according to the invention.

In all embodiments of the invention, the amount of active volatile ingredients or mixture of ingredients other than the perfume shall be from 0.5 to 2.0% by weight, and more preferably from 1.0 to 2.0% by weight of active volatile ingredient, relative to the total weight of the liquid composition.

The liquid composition may comprise further ingredients depending on the final application of the device and the skilled person is able to decide and chose those ingredients. For instance, in the case of a fine fragrance application, other ingredients may include dyes, UV filters, humectants, emollients, antibacterial agent, skincare actives, antioxidants.

The device according to the invention allows dispensing a liquid composition comprised therein at least partly in the air.

According to a particular embodiment, the liquid composition is fully dispensed in the air, and the device is an air freshener device. Air-freshening devices or deodorizers are known and used in many households to mask bad odors or to diffuse fragrances or other volatile active ingredients to the air surrounding the device, in particular in rooms and cupboards, litter containers, and other closed environments. The invention's device can take any form of known air freshener devices. Such devices dispense the fragrance or other active volatile substance into the air either as droplets which transition to vapor, or as the molecules of fragrance ingredients directly evaporating from a source. Air-freshening devices that introduce fragrance to the air as droplets include: aerosol sprays, or atomizers; wall plug-ins or battery-powered devices that employ piezoelectric technology to aerosolize the fragrance composition; and, nebulization systems which convert liquid fragrances into a vapor normally without the use of heat. Air-freshening devices that introduce fragrance to the air by direct evaporation from a source include: scented candles and devices which use a candle flame or some other heat source to heat and vaporize a fragrance formulation; incense burners; wall plug-ins which normally use heat to vaporize a liquid composition from a wick or from a gel; fragrance impregnated gels which release fragrance as the gel evaporates sometimes with the help of an electric fan; wick and reed diffusers which release fragrance by evaporation from fragrance-soaked wicks or wooden reeds; and, fragrance impregnated solid or semi-solid materials like paper, plastics, plaster and wood.

The aerosol spray uses a propellant and fragrance packaged under pressure in a sealed metal or glass container with a valve which is opened by pressing down a button which contains a spray nozzle—the actuator. When the container's valve is opened by pressing the actuator, fragrance is forced through the spray nozzle located inside the actuator to create a mist of droplets containing fragrance. The propellant may be a liquefied gas such as propane, butane or dimethyl ether; or, it may be a compressed gas such as compressed air or compressed nitrogen.

A relatively recent type of aerosol package has been developed that comprises a plastic bag filled with a liquid fragrance composition contained within a can. The bag is attached to the valve/actuator/spray nozzle and sealed in the can surrounded by air under pressure. When the actuator is pressed, the valve opens and the liquid composition is forced through the nozzle by the pressure around the bag.

Also suitable for the present invention are automatic aerosol dispenser devices for intermittently releasing a dose of an aerosol from an aerosol can to the surroundings. These devices generally comprise a housing, which comprises: an aerosol container containing the fragrance solution under pressure; a release mechanism adapted to release the dose of aerosol from the can to the environment when actuated; an outlet connected to the aerosol release mechanism permitting the releasing of the dose of aerosol through the housing; an actuating mechanism adapted to actuate the aerosol release mechanism intermittently; and, a timing mechanism for controlling the interval of time between actuations.

The atomizer comprises a plastic, glass or metal container of fragrance solution and a pump actuator. This operates in a similar fashion to an aerosol but the liquid fragrance composition is not packed under pressure. The pressure to atomize/aspirate the fragrance solution is created by the user of the product pressing the pump or pulling a trigger. This action creates sufficient pressure to draw the liquid stored in the container through a tube and into the actuator and spray nozzle. The mist created comprises droplets that are generally larger than those created using an aerosol spray device.

Piezoelectric technology is one of a number of electromechanical processes that exist for the generation of droplets. One method for such distribution is to atomize a liquid by a device comprising a perforated structure which is vibrated by an electromechanical transducer which has a composite thin-walled or planar structure, and is arranged to operate in a bending mode. Liquid is supplied to the vibrating perforated structure and sprayed therefrom in droplets upon vibration of the perforated structure.

Nebulizing scent delivery devices comprise an atomizer to atomize a liquid fragrance oil into a scented mist and deliver the scented mist to air outside of the atomizer.

Also suitable to the invention are a large variety of plug-in electrical devices that evaporate a fragrance composition into the surrounding air. Generally, these devices consist of a perfume or fragrance composition; an electrical heater; and, a power supply. By the application of heat to the perfume or fragrance source, there is a continuous supply of the perfume or fragrance to the space in which the device is placed According to particular embodiment, the device according to the invention is an air-freshener selected from the group consisting of an aerosol air freshener, an automatic aerosol air freshener spray and a liquid electrical air freshener.

According to an embodiment, the device of the invention consists of a spraying device.

When the device according to the invention is an air-freshener, the amount of perfume in the liquid composition is such that the ratio between the perfume and the at least one Formula Compound is comprised between 5000:1 and 50:1, preferably between 2000:1 and 100:1; more preferably between 1000:1 and 200:1.

According to a further embodiment, the device is in the form of a perfume, an eau de parfum, eau de cologne, deo-cologne, body splash, body spray, deodorant or antiperspirant dispensing device. Preferably the dispensing device is a spraying device. Preferably the spraying device is selected within the group of natural sprays, aerosols and piezo-electric devices.

When the device according to the invention is in the form of a perfume, an eau de toilette, eau de parfum or eau de cologne, a body splash or a body spray the amount of perfume in the liquid composition is such that the ratio between the perfume and the at least one Formula Compound is comprised between 50000:1 and 150:1, preferably between 25000:1 to 500:1 and more preferably between 15000:1 to 1000:1.

When the device is in the form of a personal deodorant or antiperspirant, the ratio between the perfume and the at least one Formula Compound is comprised between 5000:1; preferable between 1250:1; more preferably between 250:1.

The liquid composition might include further functional ingredients depending on the application. These ingredients do not warrant a more detailed description here, which would in any case not be exhaustive. The skilled person is capable of selecting them on the basis of general knowledge in the art and the desired characteristics of the liquid composition to be dispensed.

In another aspect, the invention provides a method to enhance, improve and/or modulate the sensorial perception of a perfuming composition to be dispensed at least partly in the air or of a perfumed article containing said perfuming composition, which method comprises adding to said composition or article an effective amount of at least a Formula Compound. In a preferred embodiment the at least one Formula Compound is added in an amount comprised between 0.0005 and 0.2%, preferably between 0.001 to 0.1%; more preferably between 0.002 and 0.01% % by weight of the liquid composition % by weight of the finished product formulation.

According to a further embodiment, the invention also provides a method to improve the fragrance diffusion from a source in the air of a perfuming composition or a perfumed article which method comprises adding to said composition an effective amount of at least one "formula compound" as defined in the present invention.

A liquid composition suitable for being delivered in the air via an emanating device comprising (i) at least one "formula compound" as defined in the present invention in an amount comprised between 0.0005 and 0.2%, preferably between 0.001 to 0.1%; more preferably between 0.002 and 0.01% % by weight of the liquid composition and (ii) at least one perfume oil;

is another object of the present invention. The nature of the composition and perfume is similar to what has been described above.

All embodiments of the device according to the invention can be prepared according to the known and standard processes, wherein the use of preferred ingredients and relative proportions thereof, as defined in previous sections of this description, make it possible to obtain a variety of devices with advantageous properties.

The invention will now be described in further detail by way of the following examples wherein the amounts are indicated in % by weight, relative to the weight of the gel, and the temperatures are indicated in degrees centigrade.

Example 1

Standard Aerosol Air Freshener Device According to the Invention

An aerosol air freshener according to the invention was prepared with the following ingredients.

TABLE 1

| Ingredient | Amount (% by weight) |
| --- | --- |
| Deionized water | 69.20 |
| Solubiliser [1] | 0.60 |
| Fragrance [2] | 0.37 |
| N-(1H-pyrazol-5-yl)-N-(thiophen-2-ylmethyl)-2-(p-tolyloxy)acetamide solution [3] | 0.13 |
| Butane propellant | 29.70 |
| TOTAL | 100.00 |

[1] Sorbitan Mono-oleate
[2] see Table 2 below
[3] 1% N-(1H-pyrazol-5-yl)-N-(thiophen-2-ylmethyl)-2-(p-tolyloxy)acetamide in solvent PG

TABLE 2

| Ingredient | Amount (parts by weight) |
| --- | --- |
| BENZYL ACETATE | 100.000 |
| HEXYL ACETATE | 30.000 |
| BENZALDEHYDE | 4.000 |
| CINNAMIC ALDEHYDE | 9.000 |
| ALDEHYDE MNA | 4.000 |
| ETHYL 2-METHYL-PENTANOATE [1] | 20.000 |
| NONALACTONE GAMMA | 15.000 |
| 4-(4-HYDROXY-1-PHENYL)-2-BUTANONE | 20.000 |
| COUMARIN | 35.000 |
| DIPG MONOMETHYLETHER | 600.000 |
| DOWANOL TPM | 600.000 |
| ETHYL PRALINE | 20.000 |
| ETHYL VANILLIN | 40.000 |
| *EUCALYPTUS* OIL | 5.000 |
| FRESKOMENTHE | 75.000 |
| CLOVE OIL | 6.000 |
| HEDIONE HC ® [2] | 9.000 |
| 2,6-DIMÉTHYL-5-HEPTANAL [3] | 4.000 |
| MINT ARVENSIS OIL | 35.000 |
| ETHYLMETHYLPHENYLGLYCIDATE | 95.000 |
| NUSSOL EXTRA | 1.000 |
| UNDECAVERTOL ® [3'] | 5.000 |
| VANILLIN | 19.000 |
| VERDOX ™ [4] | 95.000 |
| 2,4-DIMETHYL-3-CYCLOHEXENE-1-CARBALDEHYDE [5] | 10.000 |

[1] Origin: Firmenich SA, Geneva, Switzerland
[2] Methyl dihydrojasmonate; Origin: Firmenich SA, Geneva, Switzerland
[3] Origin: Givaudan SA, Vernier, Switzerland
[3'] 4-methyl-3-decen-5-ol, Givaudan SA, Vernier, Switzerland
[4] 2-tert-butyl-1-cyclohexyl acetate; Origin: International Flavors & Fragrances, USA
[5] Origin: Firmenich SA, Geneva, Switzerland A premix was prepared in two steps. In the first step, a solution comprising approximately 1% by weight of N-(1H-pyrazol-5-yl)-N-(thiophen-2-ylmethyl)-2-(p-tolyloxy)acetamide in Propylene Glycol (Solvent PG) was made. In the second step, 0.37 g of fragrance base was admixed with 0.60 g of solubiliser and 0.13 g of the 2% N-(1H-pyrazol-5-yl)-N-(thiophen-2-ylmethyl)-2-(p-tolyloxy)acetamide solution previously prepared, in a glass bottle.

Approximately 69.20 g of deionised water and 1.10 g of the above premix were added to the aerosol can and a valve sealed (crimped) to the can. The can was then pressurized with approximately 29.70 g of butane propellant and the actuator fitted to the valve stem.

Example 2

Automatic Aerosol Air Freshener According to the Invention

An automatic aerosol air freshener according to the invention was prepared with the following ingredients

TABLE 3

| Ingredient | Amount (% by weight) |
| --- | --- |
| Ethanol | 55.75 |
| DI water | 6.00 |
| Butane Propellant | 36.00 |
| Fragrance [1] | 2.02 |
| N-(1H-pyrazol-5-yl)-N-(thiophen-2-ylmethyl)-2-(p-tolyloxy)acetamide solution [2] | 0.23 |
| TOTAL | 100.00 |

[1] see Table 2 from Example 1
[2] 2% N-(1H-pyrazol-5-yl)-N-(thiophen-2-ylmethyl)-2-(p-tolyloxy)acetamide in dipropyleneglycol n-propyl ether (Dowanol ® DPnP, trademark and origin: Dow)

A premix was prepared in two steps. In the first step, a solution comprising approximately 2% by weight of N-(1H-pyrazol-5-yl)-N-(thiophen-2-ylmethyl)-2-(p-tolyloxy)acetamide in dipropyleneglycol n-propyl ether (Dowanol® DPnP, trademark and origin: Dow) was made. In the second step, 2.02 g of fragrance base was admixed with 0.23 g of the 2% N-(1H-pyrazol-5-yl)-N-(thiophen-2-ylmethyl)-2-(p-tolyloxy)acetamide solution previously prepared, in a glass bottle. The resulting liquid composition comprised approximately 90% by weight of fragrance base, 9.8% by weight Dowanol® DPnP and 0.2% by weight N-(1H-pyrazol-5-yl)-N-(thiophen-2-ylmethyl)-2-(p-tolyloxy)acetamide.

Approximately 55.75 g of ethanol and 6.00 g of deionized water were added to the aerosol can. Then, 2.25 g of premix was added to the can and a metered-dose valve sealed (crimped) to the can. The can was then pressurized with approximately 36.00 g of butane propellant and the actuator fitted to the valve stem. The aerosol can was then placed into an automatic spray unit, capable of automatically dispensing a controlled amount of product in the air at regular, predefined intervals.

Example 3

Liquid Electrical Air Freshener According to the Invention

A liquid electrical air freshener was prepared with the following ingredients:

TABLE 4

| Ingredient | Amount (% by weight) |
| --- | --- |
| Fragrance [1] | 90.00 |
| N-(1H-pyrazol-5-yl)-N-(thiophen-2-ylmethyl)-2-(p-tolyloxy)acetamide solution [2] | 10.00 |
| Total | 100.00 |

[1] See Table 2 from Example 1
[2] 2% N-(1H-pyrazol-5-yl)-N-(thiophen-2-ylmethyl)-2-(p-tolyloxy)acetamide in dipropyleneglycol n-propyl ether (Dowanol ® DPnP, trademark and origin: Dow)

In the first step, a solution comprising approximately 2% by weight of N-(1H-pyrazol-5-yl)-N-(thiophen-2-ylmethyl)-

2-(p-tolyloxy)acetamide in dipropyleneglycol n-propyl ether (Dowanol® DPnP, trademark and origin: Dow) was made. In the second step, 18.0 g of fragrance base was admixed with 2.0 g of the 2% N-(1H-pyrazol-5-yl)-N-(thiophen-2-ylmethyl)-2-(p-tolyloxy)acetamide solution previously prepared, in a glass bottle. The resulting liquid composition comprised approximately 90% by weight of fragrance base, 9.8% by weight Dowanol® DPnP and 0.2% by weight N-(1H-pyrazol-5-yl)-N-(thiophen-2-ylmethyl)-2-(p-tolyloxy)acetamide. This was then added to a bottle with wick inserted and placed into an electrical air freshener device.

Example 4

Air Freshener Aerosol According to the Invention

A premix was prepared in two steps. In the first step, a solution comprising approximately 2% by weight of N-(1H-pyrazol-5-yl)-N-(thiophen-2-ylmethyl)-2-(p-tolyloxy)acetamide in dipropyleneglycol n-propyl ether (Dowanol® DPnP, trademark and origin: Dow) was prepared by admixing 0.967 g of N-(1H-pyrazol-5-yl)-N-(thiophen-2-ylmethyl)-2-(p-tolyloxy)acetamide with 47.374 g of Dowanol® DPnP in a 60 ml glass bottle. In the second step, 17.831 g of fragrance base (see Table 5 below) was admixed with 1.980 g of the 2% N-(1H-pyrazol-5-yl)-N-(thiophen-2-ylmethyl)-2-(p-tolyloxy)acetamide solution previously prepared, in a 30 ml glass bottle. The resulting liquid composition comprised approximately 90% by weight of fragrance base, 9.8% by weight Dowanol® DPnP and 0.2% by weight N-(1H-pyrazol-5-yl)-N-(thiophen-2-ylmethyl)-2-(p-tolyloxy)acetamide.

TABLE 5

| INGREDIENT | % BY WEIGHT |
| --- | --- |
| ALDEHYDE C 10 | 0.30 |
| ALDEHYDE C 8 | 0.30 |
| ALPHA IRONE | 0.60 |
| CINNAMIC ALDEHYDE | 10.00 |
| DELTA DODECALACTONE | 1.00 |
| DIPROPYLENE GLYCOL | 47.30 |
| ETHYLPRALINE | 2.00 |
| ETHYLVANILLINE | 10.00 |
| EUCALYPTOL | 2.00 |
| EUGENOL | 7.50 |
| GAMMA NONALACTONE | 5.00 |
| GERANIOL | 1.50 |
| LINALOL | 4.00 |
| LINALYL ACETATE BJ | 3.00 |
| MUSCADE OIL | 0.50 |
| OCTALACTONE | 1.00 |
| SULFUROL | 0.50 |
| TERPINYL ACETATE | 3.50 |
|  | 100.00 |

Aerosol formulations were prepared using the above mentioned premix, according to the compositions described in Table 6 (values shown are in % by weight).

TABLE 6

| Ingredient | Amount (% by weight) |
| --- | --- |
| Premix | 2.25 |
| Ethanol | 55.75 |
| Deionized water | 6.00 |
| Butane propellant | 36.00 |
| TOTAL | 100.00 |

Approximately 55.75 g of ethanol and 6.00 g of deionized water were added to the aerosol can. Then, 2.25 g of premix were added to the can and a metered-dose valve sealed (crimped) to the can. The can was then pressurized with approximately 36.00 g of butane propellant and the actuator fitted to the valve stem. The aerosol can was then placed into an automatic spray unit, capable of automatically dispensing a controlled amount of product in the air at regular, pre-defined intervals.

Example 5

Preparation of a Control Air Freshener Aerosol—Outside the Scope of the Invention A control premix was prepared by admixing 18.22 g of fragrance base (composition from Table 5 from Example 4) with 2.02 g of dipropyleneglycol n-propyl ether (Dowanol® DPnP; trademark and origin: Dow) in a 30 ml glass bottle. The resulting liquid composition comprised approximately 90% by weight of fragrance base and 10% by weight of dipropyleneglycol n-propyl ether.

The process described in Example 4 was repeated, using the ingredients in the table 7 below, in the proportions indicated.

TABLE 7

| Ingredient | Amount (% by weight) |
| --- | --- |
| Control Premix | 2.25 |
| Ethanol | 55.75 |
| Deionized water | 6.00 |
| Butane Propellant | 36.00 |
| TOTAL | 100.00 |

Example 6

Sensory Evaluation of the Performance of the Device According to the Invention The performance of a device according to the invention was evaluated in sensory evaluation cabins by untrained assessors. The air freshener device used in this study was that described in Examples 4 and 5, namely an automatic aerosol capable of dispensing a controlled amount of product into the air at predefined intervals. In particular the unit was set to spray a dose every 9 minutes. The air freshener according to the invention described in example 4 was compared to a control as described in example 5.

In order to avoid cross-adaptation effects that can occur with olfactively similar stimuli, the test products were compared independently against two reference products prepared according to the same process and with same composition except that the nature of the perfume was different. The composition of the reference fragrances are described in Table 8 and Table 9.

TABLE 8

Reference fragrance 1

| Ingredient | Amount (parts by weight) |
|---|---|
| ANISALDEHYDE | 20.000 |
| BENZALDEHYDE | 40.000 |
| CINNAMIC ALDEHYDE | 35.000 |
| DIPG MONOMETHYL ETHER | 800.000 |
| ETHYL PRALINE | 50.000 |
| ETHYL VANILLIN | 10.000 |
| HELIOTROPIN [1] | 6.000 |
| NUSSOL EXTRA | 1.000 |
| ORANGE OIL | 15.000 |
| VANILLIN | 5.000 |
| ETHYL CAPROATE | 36.000 |
| HEXYL ACETATE | 15.000 |
| HEXYL ISOBUTYRATE | 12.000 |
| ETHYL BUTYRATE | 2.000 |
| AMYL VALERIANATE | 22.000 |
| VERDOX ™ [2] | 8.000 |
| CLOVE FT OIL | 4.000 |
| CUMINIC ALDEHYDE | 3.000 |
| ETHYL ISOBUTYRATE | 20.000 |
| 4-(4-HYDROXY-1-PHENYL)-2-BUTANONE | 20.000 |
| BORNYL ACETATE | 2.000 |
| BORNEOL | 5.000 |
| CITRAL | 60.000 |
| LIMONENE | 14.000 |
| NEROL | 23.000 |
| CORANOL [2'] | 10.000 |
| ISOBORNYL ACETATE | 5.000 |
| BENZYL ACETATE | 25.000 |
| DAMASCONE ALPHA | 1.000 |
| ETHYL BENZOATE | 50.000 |
| METHYLPHENYLGLYCIDATE | 5.000 |
| FRUCTONE [3] | 5.000 |
| PIPOL ACETATE | 3.000 |
| 2,4-DIMETHYL-3-CYCLOHEXENE-1-CARBALDEHYDE [4] | 5.000 |

[1] Origin: Firmenich SA, Geneva, Switzerland
[2] 2-tert-butyl-1-cyclohexyl acetate; Origin: International Flavors & Fragrances, USA
[2'] 4-cyclohexyl-2-methyl-2-butanol, Origin: Firmenich SA, Geneva, Switzerland
[3] Origin: Firmenich SA, Geneva, Switzerland
[4] Origin: Firmenich SA, Geneva, Switzerland

TABLE 9

Reference fragrance 2

| Ingredient | % by weight |
|---|---|
| ISOBORNYL ACETATE | 0.10 |
| DECANAL | 0.30 |
| AMBROX ® [1] | 0.25 |
| ANISALDEHYDE | 0.25 |
| 2,5-DIOXACYCLOHEXA-DECANE 1,6 DIONE | 0.10 |
| BACDANOL [2] | 0.90 |
| BENZYL ACETATE | 14.40 |
| BENZYL ALCOHOL | 11.50 |
| CARYOPHYLLENE | 0.10 |
| CASHMERAN ® [3] | 0.60 |
| CEDRAMBER [4] | 2.30 |
| COUMARIN | 0.90 |
| CYCLOGALBANATE [5] | 0.10 |
| ETHYL PRALINE | 0.30 |
| ETHYL VANILLIN | 1.70 |
| ETHYLENE BRASSYLATE | 1.10 |
| EUGENOL | 0.30 |
| FLORALOZONE [6] | 0.30 |
| HEDIONE ® [7] | 1.40 |
| HELIOTROPIN [8] | 0.90 |
| ISO E SUPER [9] | 1.40 |
| ISONONYL ACETATE | 12.00 |
| ISORALDEINE | 0.90 |
| LIMONENE | 0.90 |
| LINALOOL | 21.80 |
| LINALYL ACETATE | 8.60 |
| METHYLNAPHTHYLKETONE | 0.10 |
| MOUSSE CRISTAL | 0.10 |
| PINENE (MIXTURE OF ISOMERS) | 0.15 |
| cis-3-HEXENYL ACETATE | 0.15 |
| cis-3-HEXENYL BENZOATE | 0.10 |
| cis-3-HEXENYL SALICYLATE | 0.30 |
| STYRALLYL ACETATE | 0.90 |
| gamma-TERPINENE | 0.20 |
| TRIMOFIX | 0.90 |
| gamma-UNDECALACTONE | 0.10 |
| VANILLIN | 2.90 |
| VERDYL ACETATE | 4.60 |
| beta-IONONE | 5.80 |
| 2,4-DIMETHYL-3-CYCLOHEXENE-1-CARBALDEHYDE | 0.30 |

[1] (−)-(8R)-8,12-epoxy-13,14,15,16-tetranorlabdane, Origin: Firmenich SA, Geneva, Switzerland
[2] 2-éthyl-4-(2,2,3-triméthyl-3-cyclopentèn-yl)-2-butèn-1-ol, Origin: International Flavors & Fragrances, USA
[3] 1,2,3,5,6,7-hexahydro-1,1,2,3,3-pentamethyl-4-indenone, Origin: International Flavors & Fragrances, USA
[4] 8-Methoxy-2,6,6,8-tetramethyl-tricyclo[5.3.1.0(1,5)]undecane
[5] (cyclohexyloxy)-acétate d'allyle, Origin: Dragoco, Holzminden, Allemagne
[6] 3-(4/2-Ethylphenyl)-2,2-dimethylpropanal, Origin: International Flavors & Fragrances, USA
[7] Methyl dihydrojasmonate, Origin: Firmenich SA, Geneva, Switzerland
[8] 1,3-Benzodioxole-5-carbaldehyde, Origin: Firmenich SA, Geneva, Switzerland
[9] 1-(octahydro-2,3,8,8-tetramethyl-2-naphtalenyl)-1-ethanone, Origin: International Flavors & Fragrances, USA Evaluation of the test product, with and without the modulating compound, was conducted in 800 ft$^3$ evaluation cabins. In the first test, the test product without modulating compound (control from example 5) was compared to the two reference products. In the second test, the test product with modulating compound (example 4) was tested against the two reference products.

The samples were assessed by a panel of 60 untrained assessors. By "untrained assessors" we mean users of air fresheners who have not received formal olfactive training but who are used to participating in fragrances assessments and have experience in rating the perfume attributes.

The test products were placed into 800 ft$^3$ evaluation rooms one hour prior to commencement of the test. The products were hidden from view and each evaluation room was labelled with a randomly generated 3 digit code. Sample presentation was blind, balanced, randomized and sequential monadic. Assessors were directed to enter an evaluation room and wait for 60 seconds before proceeding to answer a series of questions relating to the odor they perceived in the room. After completing all questions in one room, the assessors were directed to a second evaluation room to answer and identical series of questions. Finally the assessors were directed to the third room, and again asked to complete an identical questionnaire. The assessors were asked to rate the odor according to the following attributes: fragrance liking; purchase intent (i.e. how likely they would be to purchase a product comprising the odor); uniqueness; true-to-life; multi-layered; multi-sensorial fragrance experience; refreshing; and, comforting. Fragrance liking was assessed using a 6 point scale where 1=do not like the fragrance at all and 6=like the fragrance very much. All other attributes for each sample were assessed using a scale of 1 to 5, where 1=the odor does not fit this attribute at all and 5=the odor fits the attribute extremely well.

The data generated from the panel's evaluations was statistically analyzed in each case using variance analysis (ANOVA) with Duncan's post-hoc analysis ($\alpha$=0.10).

Results of Test 1 are shown in Table 10. A letter above the value indicates that a statistical difference exists (at the 90% confidence level) between the products for that attribute. Products sharing the same letter do not differ statistically from one another.

TABLE 10

|  | Reference Product: Fragrance 1 | Reference Product: Fragrance 2 | Control without Modulating Compound |
|---|---|---|---|
| Fragrance Liking (6 point scale) | 4.18 | 3.92 | 3.83 |
| Purchase Intent (5 point scale) | a<br>3.58 | b<br>3.20 | ab<br>3.27 |
| Uniqueness | b<br>3.00 | ab<br>3.18 | a<br>3.24 |
| True-to-life | 3.67 | 3.68 | 3.71 |
| Multi-layered | 3.88 | 3.68 | 3.91 |
| Multi-sensorial fragrance experience | 3.86 | 3.77 | 3.85 |
| Refreshing | a<br>3.58 | ab<br>3.27 | b<br>2.98 |
| Comforting | 3.74 | 3.53 | 3.74 |

No statistically significant difference was found between the samples for the following attributes: fragrance liking; true-to-life; multi-layered; multi-sensorial; and, comforting. The test sample was not significantly different to the reference products for purchase intent, though the reference products did differ significantly from one another. The test product was rated significantly higher than one reference product for uniqueness. The reference product was rated as significantly lower than one reference product for refreshing.

Results of Test 2 are shown in Table 11: A letter above the value indicates that a statistical difference exists (at the 90% confidence level) between the products for that attribute. Products sharing the same letter do not differ statistically from one another.

TABLE 11

|  | Reference Product: Fragrance 1 | Reference Product: Fragrance 2 | Test Product with Modulating Compound |
|---|---|---|---|
| Fragrance Liking (6 point scale) | ab<br>4.17 | b<br>4.00 | a<br>4.44 |
| Purchase Intent (5 point scale) | ab<br>3.44 | b<br>3.33 | a<br>3.78 |
| Uniqueness | b<br>2.94 | b<br>3.17 | a<br>3.71 |
| True-to-life | b<br>3.79 | b<br>3.49 | a<br>4.21 |
| Multi-layered | b<br>3.65 | b<br>3.68 | a<br>4.27 |
| Multi-sensorial fragrance experience | b<br>3.48 | b<br>3.56 | a<br>4.08 |
| Refreshing | 3.24 | 3.32 | 3.21 |
| Comforting | a<br>3.86 | b<br>3.43 | a<br>4.16 |

The results are markedly different from those of Test 1. Surprisingly, the addition of less than 0.005% by weight of the modulating compound resulted in a very different assessment of the test product relative to the reference products. The fragrance liking and purchase intent of the test product with modulating compound was significantly higher than one of the reference products. The test product was rated significantly higher than both reference products for the following attributes: uniqueness; true-to-life; multi-layered; and, multi-sensorial fragrance experience.

Example 7

Effect of N-(1H-pyrazol-5-yl)-N-(thiophen-2-ylm-ethyl)-2-(p-tolyloxy)acetamide on Perfume Perception Emanating from an Air Freshener Device According to the Invention Assessed by Expert Evaluators The effect of the modulating compound in an air freshener was evaluated in sensory evaluation cabins by six expert fragrance evaluators. By "expert fragrance evaluators" we mean fragrance industry professionals that are recognized for their skill in the art assessing and describing fragrances. A perfumer is an example of an expert fragrance evaluator. A perfumer, sometimes referred to as a "Nose", is an expert at creating perfume compositions. Perfumers possess an acute knowledge of, and an ability to describe, a large variety of fragrance ingredients and the quality of their odors; they are also able to distinguish each of the fragrance ingredients whether alone or in combination with other fragrances. Historically, perfumers learned their craft as apprentices under the supervision of more senior perfumers in the company of their employment; many worked as a perfume technician (responsible for blending formulas) or as a chemist. Apprenticeships of this type would typically last from three to five years. More recently professional schools have been opened to the public that offer formal training courses in perfumery. ISIP (Institut supérieur international du parfum) was founded in 1970 and became Group ISIPCA (Institut supérieur international du parfum, de la cosmétique et de l'aromatique alimentaire) in 1984. ISIPCA is a school for post-graduate studies in perfume, cosmetics products and food flavor formulation, with an apprenticeship period in the fragrance and flavor industry.

The air freshener device used in this study was of the automatic aerosol type (Airwick® Freshmatic); such devices are capable of automatically dispensing a controlled amount of product into the air at regular, predefined intervals.

Premix 3 (without modulating compound) was prepared by admixing 15.456 g of fragrance base (Table 12) with 1.716 g of dipropyleneglycol n-propyl ether (Dowanol® DPnP; origin and trademark: Dow) in a 30 ml glass bottle. The resulting liquid composition comprised approximately 90% by weight of fragrance base and 10% by weight Dowanol® DPnP.

Premix 4 (with modulating compound) was prepared by admixing 19.987 g of fragrance base (Table 12) with 2.221 g of the 2% N-(1H-pyrazol-5-yl)-N-(thiophen-2-ylmethyl)-2-(p-tolyloxy)acetamide solution (prepared in Example 4 above), in a 30 ml glass bottle. The resulting liquid composition comprised approximately 90% by weight of fragrance base, 9.8% by weight Dowanol® DPnP and 0.2% by weight N-(1H-pyrazol-5-yl)-N-(thiophen-2-ylmethyl)-2-(p-tolyloxy)acetamide.

Aerosol formulations were prepared using the above mentioned premixes, according to the compositions described in Table 13 (values shown are percent by weight).

TABLE 12

| Ingredient | Amount (parts by weight) |
| --- | --- |
| CALONE ® [1] | 2.000 |
| DAMASCONE ALPHA | 7.000 |
| ETHYL 2 METHYLBUTYRATE | 20.000 |
| ALDEHYDE C 10 | 3.000 |
| ALDEHYDE MNA | 6.000 |
| BENZYL ACETATE | 80.000 |
| CETALOX ® [2] | 4.000 |
| CITRONELLYL NITRILE | 5.000 |
| CYCLOSAL | 6.000 |
| DIHYDROMYRCENOL PURE | 68.000 |
| FRUCTONE ® [3] | 40.000 |
| HEDIONE HC ® [4] | 10.000 |
| BETA IONONE LINALOL BJ | 8.000 |
| 2,6-DIMÉTHYL-5-HEPTANAL [5] | 35.000 |
| ROSE OXIDE | 3.000 |
| UNDECALACTONE GAMMA | 1.000 |
| VERDYL ACETATE | 19.000 |
| VERDYL PROPIONATE | 23.000 |
| ALDEHYDE C 8 | 7.000 |
| CITRAL [6] | 2.000 |
| 2,4-DIMETHYL-3-CYCLOHEXENE-1-CARBALDEHYDE [7] | 8.000 |
| CEDARWOOD OIL VIRGINIA | 9.000 |
| ISORALDEINE 70 P | 4.000 |
| ETHYL 2-METHYL-PENTANOATE [8] | 11.000 |
| HELVETOLIDE ® [9] | 18.000 |
| AMBER CORE | 5.000 |
| ALLYL CAPROATE | 5.000 |
| ISOPAR M | 12.000 |
| DIPG MONOMETHYL ETHER | 280.000 |
|  | 300.000 |

[1] 7-Methyl-2H,4H-1,5-benzodioxepin-3-one, Origin: Firmenich SA, Geneva, Switzerland
[2] dodecahydro-3a,6,6,9a-tetramethyl-naphtho[2,1-b]furan, Origin: Firmenich SA, Geneva, Switzerland
[3] 2-méthyl-1,3-dioxalane-2-acétate d'éthyle, Origin: International Flavors & Fragrances, USA
[4] Methyl dihydrojasmonate, Origin: Firmenich SA, Geneva, Switzerland
[5] Origin: Givaudan SA, Vernier, Switzerland
[6] Origin: Firmenich SA, Geneva, Switzerland
[7] Origin: Firmenich SA, Geneva, Switzerland
[8] Origin: Firmenich SA, Geneva, Switzerland
[9] (1S,1'R)-2-[1-(3',3'-dimethyl-1'-cyclohexyl)ethoxy]-2-methylpropyl propanoate, Origin: Firmenich SA, Geneva, Switzerland

TABLE 13

| Ingredient | Test Product without Modulating Compound | Test Product with Modulating Compound | Reference Product without Modulating Compound |
| --- | --- | --- | --- |
| Premix 3 | 2.25% | — | — |
| Premix 4 | — | 2.25% | — |
| Ethanol | 55.75% | 55.75% | 55.75% |
| Deionized water | 6.00% | 6.00% | 6.00% |
| Butane Propellant | 36.00% | 36.00% | 36.00% |
|  | 100.00% | 100.00% | 100% |

Approximately 55.75 g of ethanol and 6.00 g of deionized water were added to the aerosol can. Then, 2.25 g of fragrance base or premix was added to the can and a metered-dose valve sealed (crimped) to the can. The can was then pressurized with approximately 36.00 g of butane propellant and the actuator fitted to the valve stem. The aerosol can was then placed into the automatic spray unit, and the unit set to spray a dose every 9 minutes. The test products were placed into 800 ft³ evaluation rooms one hour prior to commencement of the evaluations. The products were hidden from view and each evaluation room was labelled with a randomly generated 3 digit code. An expert evaluator was directed to enter one evaluation room and instructed to remain in the room for 5 minutes. After 5 minutes the evaluator left the room and waited in an odor-free environment for approximately 10 minutes. He/she was then directed to the second evaluation room and asked to remain there f or 5 minutes. Upon leaving the second chamber the evaluator was interviewed and asked to describe the similarities and differences between the odors in the two rooms. Six expert fragrance evaluators participated in the test; three of them assessed the product without the modulating compound first; the other three assessed the product with the modulating compound first. There was consensus among the expert evaluators that the presence of less than 0.005% by weight of the modulating compound altered the perceptual characteristics of the perfume product: the olfactive quality of fragrance was maintained but the overall sensorial experience was enhanced. A non-exhaustive list of descriptors used to describe the positive differences between the two test products included:

Sweeter and lighter;
More citrus and clean;
More multi-layered, fresh and unique;
Lighter;
Lighter, softer, more airy, more refreshing, sweeter, more edible;
More fruity, floral, cleaner, lighter and fresher;
Lighter and more refreshing;
Soft, fresh, watery;
Clean and airy;
Invigorating;
Fruity, sweet, fresh;
Fresh, mountain airy; and,
Subtle, light, refreshing.

The consensus opinion was that the product comprising fragrance in combination with the modulating compound provided a cleaner, lighter, fresher and more airy sensorial experience than the product comprising fragrance only. This is viewed by the experts as a positive benefit that would enhance the overall consumer experience.

Example 8

Spraying Device According to the Invention

One perfume, intended to form the fragrance component of the device of the invention, was prepared by admixing the following ingredients, in the amounts indicated in the Table 14 below.

TABLE 14

| Fragrance I | |
| --- | --- |
| Fragrance I Ingredients | (Parts by weight) |
| Limonene | 368 |
| Cis-3-Hexenol | 3 |
| 2,4-Dimethyl-3-cyclohexene-1-carbaldehyde | 10 |
| Aphermate[3] 10% DIPG | 10 |
| Sclareolate ®* [1] | 90 |
| Linalol | 79 |
| 3-Methoxy-7,7-dimethyl-10-methylene-bicyclo[4.3.1]decane* | 53 |
| Damascone Alpha* 10% DIPG | 13 |
| Coranol | 53 |
| Cedramber[2] | 50 |
| Cyclosal | 5 |
| Decal | 3 |
| Gamma-Undecalactone* | 3 |
| Ambrox ®* | 3 |

TABLE 14-continued

Fragrance I

| Fragrance I Ingredients | (Parts by weight) |
|---|---|
| Lilial ® | 18 |
| (Methoxymethoxy)Cyclododecane | 26 |

*origin: Firmenich SA, Geneva, Switzerland
[1] Propyl (S)-2-(1,1-dimethylpropoxy)propanoate
[2] 8-Methoxy-2,6,6,8-tetramethyl-tricyclo[5.3.1.0(1,5)]undecane
[3] 1-(3,3-dimethyl-1-cyclohexyl)ethyl formate; origin: International Flavors & Fragrances

TABLE 15

Liquid Composition A according to the invention

| Component | Composition (weight %) |
|---|---|
| Fragrance I | 10.00 |
| Ethanol 96% | 79.58 |
| N-(1H-pyrazol-5-yl)-N-(thiophen-2-ylmethyl)-2-(p-tolyloxy)acetamide @ 5.4% DIPG | 0.1 |
| Demineralised water | 10.32 |

In parallel, a blank composition was prepared by replacing N-(1H-pyrazol-5-yl)-N-(thiophen-2-ylmethyl)-2-(p-tolyloxy)acetamide, in the amount indicated in the table for Composition A, by the same amount of dipropylene glycol.

Composition A was then evaluated on a blind test against the blank, by a panel of 18 individuals. The latter were asked to evaluate the odour intensity perceived, on a scale of 1 to 10, from each pair of samples, i.e. that of the composition according to the invention and the blank. On the scale 1 to 10, 0 represented an inability to detect the odour and 10 represented a very strong odour.

The samples were evaluated after application on glass slides at distance zero and at distance 80 cm, the glass slide having been placed on a hot plate at a constant temperature of 32° C., for 30 minutes. For distance 80 cm, a compressed air blows on the glass slide towards the panellist, the panellist being placed at 80 cm from the glass slide, thanks to the apparatus called Pulscent®. The results of the blind tests thus carried out were averaged and treated for variance following Student's t-test analysis (alpha=0.05).

FIG. 1 represents the results of a blind test evaluation, after about 30 minutes at 32° C., of Composition A against the blank at distance zero and distance 80 cm. It is clearly seen from this figure that the fragrance without N-(1H-pyrazol-5-yl)-N-(thiophen-2-ylmethyl)-2-(p-tolyloxy)acetamide at distance zero is significantly stronger than the fragrance with N-(1H-pyrazol-5-yl)-N-(thiophen-2-ylmethyl)-2-(p-tolyloxy)acetamide in terms of fragrance intensity. N-(1H-pyrazol-5-yl)-N-(thiophen-2-ylmethyl)-2-(p-tolyloxy)acetamide seems to retain fragrance evaporation. On the other hand, at a distance of 80 cm, the fragrance with N-(1H-pyrazol-5-yl)-N-(thiophen-2-ylmethyl)-2-(p-tolyloxy)acetamide is significantly stronger than the fragrance without N-(1H-pyrazol-5-yl)-N-(thiophen-2-ylmethyl)-2-(p-tolyloxy)acetamide in terms of fragrance intensity. N-(1H-pyrazol-5-yl)-N-(thiophen-2-ylmethyl)-2-(p-tolyloxy)acetamide seems to improve fragrance diffusion in the air.

Example 9

Intensity Enhancing Activity of N-(1H-pyrazol-5-yl)-N-(thiophen-2-ylmethyl)-2-(p-tolyloxy)acetamide The effect of the modulating compound in an air freshener was evaluated in sensory evaluation cabins. The air freshener device used in this study was of the automatic aerosol type (Airwick® Freshmatic); such devices are capable of automatically dispensing a controlled amount of product into the air at regular, predefined intervals.

A fragrance base was prepared by admixing fragrance components in the amounts indicated in Table 16 below.

TABLE 16

Fragrance base (mango type)

| Ingredient | Amount (parts by weight) |
|---|---|
| DBE-LVP | 723.000 |
| VERDOX ™ [1] | 75.000 |
| LINALOL | 45.000 |
| HEXYL ACETATE | 25.000 |
| ALLYL CAPROATE | 22.000 |
| UNDECALACTONE GAMMA | 20.000 |
| PIPOL ACETATE | 13.000 |
| ETHYL PRALINE | 13.000 |
| ALLYL CYCLOHEXYLPROPIONATE | 9.000 |
| ETHYL 2-METHYL-PENTANOATE [2] | 7.000 |
| UNDECAVERTOL | 7.000 |
| HOMOFURONOL (10% soln. in DBE-LVP) | 5.000 |
| DECALACTONE DELTA | 5.000 |
| 2,4-DIMETHYL-3-CYCLOHEXENE-1-CARBALDEHYDE [3] | 5.000 |
| DECALACTONE | 5.000 |
| NONALACTONE GAMMA | 4.000 |
| OXANE (10% soln. in DBE-LVP) | 4.000 |
| SULFUROL (10% soln. in DBE-LVP) | 3.000 |
| OCTALACTONE G | 3.000 |
| SULFOX (1% soln. in dipropylene glycol) | 3.000 |
| DODECALACTONE CP | 2.000 |
| DIMETHYLSULFIDE (10% soln. in triethylcitrate) | 1.000 |
| OCTALACTONE DELTA | 1.000 |

[1] 2-tert-butyl-1-cyclohexyl acetate; Origin: International Flavors & Fragrances, USA
[2] Origin: Firmenich SA, Geneva, Switzerland
[3] Origin: Firmenich SA, Geneva, Switzerland A solution comprising approximately 4% by weight of N-(1H-pyrazol-5-yl)-N-(thiophen-2-ylmethyl)-2-(p-tolyloxy)acetamide in dipropyleneglycol-n-propyl ether (Dowanol® DPnP) was prepared by admixing 0.509 g of N-(1H-pyrazol-5-yl)-N-(thiophen-2-ylmethyl)-2-(p-tolyloxy)acetamide with 12.222 g of Dowanol® DPnP in a 20 ml glass vial.

Aerosol formulations were prepared according to the compositions described in Table 17 below (values shown are percent by weight).

TABLE 17

Aerosol formulations

| Ingredient | Test Aerosol without Modulating Compound | Test Aerosol with Modulating Compound |
|---|---|---|
| Fragrance base (Table 16) | 2.25% | 2.25% |
| Dowanol® DPnP | 0.225% | — |

TABLE 17-continued

Aerosol formulations

| Ingredient | Test Aerosol without Modulating Compound | Test Aerosol with Modulating Compound |
|---|---|---|
| 4% solution of N-(1H-pyrazol-5-yl)-N-(thiophen-2-ylmethyl)-2-(p-tolyloxy)acetamide in Dowanol ® DPnP | — | 0.225% |
| Ethanol | 55.525% | 55.75% |
| Deionized water | 6.00% | 6.00% |
| Butane Propellant | 36.00% | 36.00% |
| | 100.00% | 100.00% |

Approximately 55.525 g of ethanol, 6.00 g of deionized water and 2.25 g of fragrance base (Table 16) were added to each aerosol can. To one of the cans, 0.225 g of Dowanol® DPnP was added. To the other can, 0.225 g of the 4% solution of N-(1H-pyrazol-5-yl)-N-(thiophen-2-ylmethyl)-2-(p-tolyloxy)acetamide in Dowanol® DPnP prepared above was added. A metered-dose valve was sealed (crimped) to each of the cans, and both pressurized with approximately 36.00 g of butane propellant. Actuators were fitted to the valve stems, the aerosol cans were placed into automatic spray units, and both spray units set to spray a dose every 9 minutes.

Evaluation of the test aerosols, with and without the modulating compound, was conducted in 800 ft³ evaluation cabins. The samples were assessed by a panel of 25 trained assessors. A trained assessor is a person, who has been screened for olfactive acuity and who has received training in order to be able to: detect and describe characteristics present in an odor in a qualitative sense; and, detect and describe the intensity of an odor in a quantitative sense. They are thoroughly familiar with the test procedure, the questionnaire and the type of judgement required (in this case assessment of perceived odor intensity).

The test aerosols were placed into the evaluation rooms one hour prior to commencement of the test. The products were hidden from view and each evaluation room was labeled with a randomly generated 3 digit code. Sample presentation was blind, balanced, randomized and sequential monadic. Each trained assessor was directed to smell the odor in one of the evaluation rooms via a hatch in the door of the room. The assessor was asked to rate the intensity of the odor in the room by making a mark on a horizontal line on the questionnaire which corresponded to the amount of the perceived odor. The left end of the scale corresponded to "no odor" and the right end of the scale corresponded to "extremely strong odor". The assessor then closed the hatch and was instructed to wait for 60 seconds before being directed to the second room to repeat the process of intensity evaluation.

The marks from the line scales were converted to numbers on a range from 0 to 10 by measuring the position of the marks along the scales. This numerical data was statistically analyzed in each case using Student's t-test (one-tailed, alpha=0.05).

Figure 2:
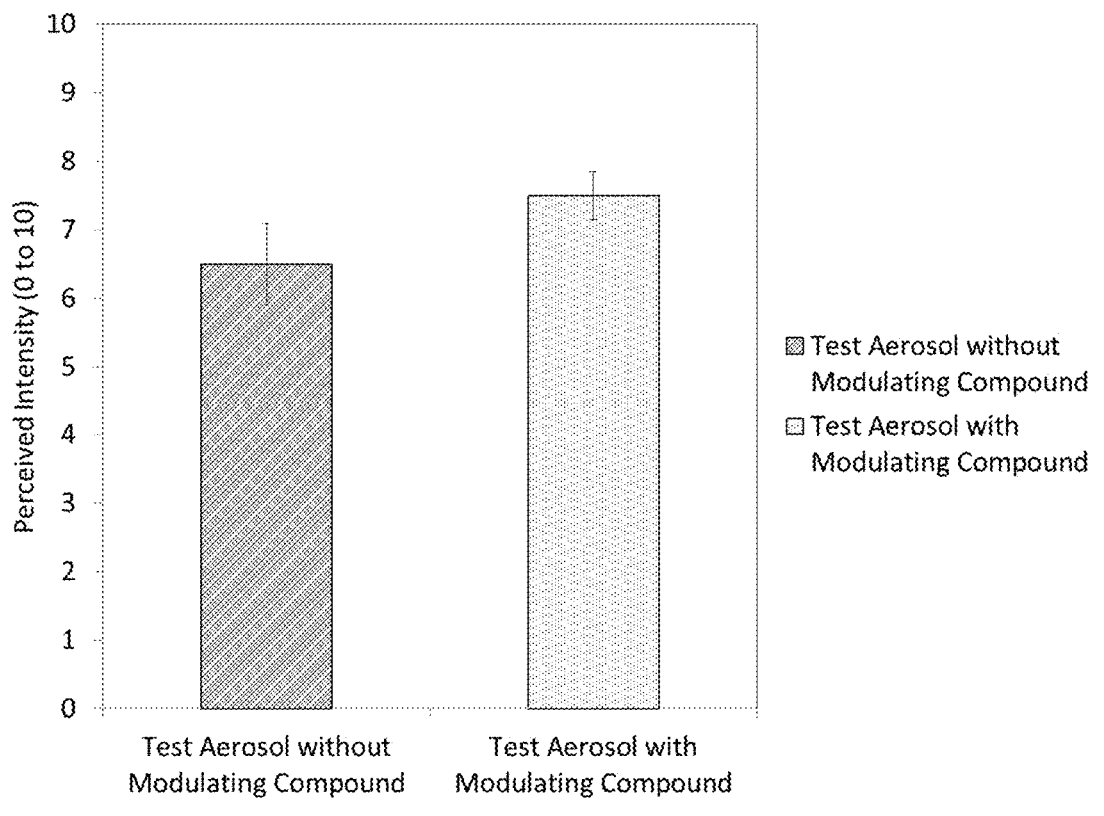

FIG. 2 represents the results of the test. It can be clearly seen that the sample comprising N-(1H-pyrazol-5-yl)-N-(thiophen-2-ylmethyl)-2-(p-tolyloxy)acetamide was perceived as having significantly higher perceived intensity than the sample without N-(1H-pyrazol-5-yl)-N-(thiophen-2-ylmethyl)-2-(p-tolyloxy)acetamide.

Example 10

One perfume, intended to form the fragrance component of compositions of the invention, was prepared by admixing the following ingredients, in the amounts indicated in the table 18 below.

TABLE 18

Fragrance II

| Fragrance II Ingredients | (Parts by weight) |
|---|---|
| ACETATE DE BENZYLE | 3 |
| ACETATE DE LINALYLE | 200 |
| ALDEHYDE C 10 | 1 |
| ALDEHYDE C 8 | 1 |
| CARVONE GAUCHE | 1 |
| CITRAL [1] | 30 |
| CITRON SFUMA | 230 |
| CITRONELLOL | 1 |
| ESTER DE POIRE NAT | 5 |
| GALBANOLENE SUPER | 1 |
| ISO E SUPER [2] | 50 |
| LAVANDE | 6 |
| LIMONENE 1 X DIST FAB | 200 |
| LINALOL BJ | 72 |
| METHYLANTHRANILATE DE METHYLE | 3 |
| PETITGRAIN | 40 |
| ROMANDOLIDE ® [3] | 50 |
| (+−)-3-méthyl-5-(2,2,3-triméthyl-3-cyclopentèn-1-yl)-2-pentanol [4] | 15 |
| TARRAGOL | 1 |

[1] Origin: Firmenich SA, Geneva, Switzerland
[2] 1-(octahydro-2,3,8,8-tetramethyl-2-naphtalenyl)-1-ethanone, Origin: International Flavors & Fragrances, USA
[3] (1S,1'R)-[1-(3',3'-Dimethyl-1'-cyclohexyl)ethoxycarbonyl]methyl propanoate, Firmenich SA, Geneva, Switzerland
[4] Givaudan SA, Vernier, Switzerland

TABLE 19

Composition B according to the invention

| Component | Composition (weight %) |
|---|---|
| Fragrance II | 10.00 |
| Ethanol 96% | 79.58 |
| N-(1H-pyrazol-5-yl)-N-(thiophen-2-ylmethyl)-2-(p-tolyloxy)acetamide @ 5.4% DIPG | 0.1 |
| Demineralised water | 10.32 |

In parallel, a blank composition was prepared by replacing N-(1H-pyrazol-5-yl)-N-(thiophen-2-ylmethyl)-2-(p-tolyloxy)acetamide, in the amount indicated in the table for Composition B, by the same amount of dipropylene glycol.

Composition B and the blank composition were assessed through a Quantitative Descriptive Analysis methodology (QDA), after application on glass slides thermostated at 32° C. during several time points: Fresh, 2 h15, 4 h15 (FIG. 3), 6 h15 (FIG. 4).

QDA is used to describe and quantify fragrance characteristics and provides a descriptive evaluation using a consensual vocabulary and a linear line scale.

8 to 12 panelists were screened and trained for complex sensory tasks. This methodology is based on iterative process to generate language terms, where attributes are derived entirely from the panelists. Attributes are then defined, and reference materials are utilized in the evaluations. Three complete replications per panelist per sample are done. QDA utilizes a 10 cm semi-structured line intensity scale which is converted to numerical values from 0-10.

The results of these blind tests thus carried out were averaged and treated for variance following Duncan's post-hoc analysis ($\alpha=0.05$).

Products sharing a letter are not consider as being significantly different from each other, see table below.

TABLE 20

Odor intensity of each attribute after a given time from application

|  | Fresh | | After 2 h 15 min | | After 4 h 15 min | | After 6 h 15 min | | ANOVA |
| --- | --- | --- | --- | --- | --- | --- | --- | --- | --- |
|  | Blank | Composition B | Blank | Composition B | Blank | Composition B | Blank | Composition B | (p=) |
| Bergamot | 4.9 AB | 5.6 A | 3.7 B | 5.9 A | 1.4 C | 4.6 AB | 1.6 C | 4.6 AB | <0.0001*** |
| Lime | 3.4 A | 3.4 A | 2.0 BC | 2.3 ABC | 0.8 D | 2.9 AB | 1.0 CD | 2.8 AB | <0.0001*** |
| Green Apple | 3.6 A | 3.1 AB | 2.3 ABC | 2.9 AB | 1.7 BC | 3.2 A | 1.2 C | 2.6 ABC | 0.0094** |
| *Freesia* | 5.0 AB | 4.7 AB | 3.2 C | 5.4 A | 1.5 D | 3.8 BC | 1.13 D | 4.4 ABC | <0.0001*** |
| Honeysuckle | 4.4 A | 4.2 A | 2.3 C | 3.9 AB | 2.4 BC | 4.0 A | 0.7 D | 3.3 ABC | <0.0001*** |
| Lilac | 2.8 AB | 2.1 ABC | 3.3 A | 3.7 A | 1.3 BC | 3.0 A | 1.0 C | 2.5 ABC | 0.0065** |
| Muguet | 3.0 A | 3.3 A | 3.4 A | 3.3 A | 1.2 B | 2.9 A | 1.0 B | 3.4 A | <0.0001*** |
| Neroli | 2.5 A | 3.2 A | 2.6 A | 3.7 A | 0.5 B | 3.2 A | 0.1 B | 3.0 A | <0.0001*** |
| Rose | 2.1 AB | 3.0 A | 2.8 A | 3.0 A | 1.6 AB | 3.0 A | 0.8 B | 1.5 AB | 0.0066** |
| Tuberose | 3.5 A | 3.0 A | 2.4 A | 2.7 A | 1.1 B | 3.1 A | 0.8 B | 2.5 A | 0.0003*** |
| Violet | 1.8 ABC | 2.0 ABC | 1.9 ABC | 2.2 AB | 0.9 BC | 2.1 ABC | 0.7 C | 2.7 A | 0.0396* |
| Watery | 2.8 A | 2.5 AB | 3.0 A | 2.9 A | 2.1 AB | 3.1 A | 1.4 B | 2.7 A | 0.0292* |
| Aldehydic | 3.1 A | 2.6 A | 2.0 AB | 2.7 A | 1.9 AB | 3.1 A | 0.9 B | 3.2 A | 0.0034** |
| Creamy | 1.8 B | 1.6 B | 3.5 A | 2.5 AB | 1.2 B | 1.6 B | 1.3 B | 1.7 B | 0.0017** |
| Lavender | 3.8 A | 3.8 A | 3.7 A | 3.2 A | 1.5 B | 3.8 A | 1.1 B | 3.7 A | <0.0001*** |
| Lemongrass | 3.9 A | 4.1 A | 1.6 BC | 2.2 B | 0.5 C | 2.3 B | 0.2 C | 2.1 B | <0.0001*** |
| Hyacinth | 1.5 | 1.4 | 0.9 | 1.6 | 0.7 | 2.0 | 0.5 | 1.5 | 0.0825# |
| Petit Grain | 2.5 AB | 3.3 A | 2.1 AB | 2.7 AB | 0.8 CD | 2.0 BC | 0.3 D | 2.2 AB | <0.0001*** |
| Musk | 3.2 A | 3.1 A | 3.1 A | 3.6 A | 1.6 B | 3.5 A | 1.6 B | 3.4 A | 0.0011** |
| Fougere | 3.4 A | 4.5 A | 3.0 A | 4.0 A | 1.4 B | 3.6 A | 1.2 | 3.8 A | <0.0001*** |
| Forest Moss | 4.8 A | 4.4 A | 4.1 A | 4.6 A | 1.5 B | 4.2 A | 0.9 B | 3.4 A | <0.0001*** |
| Cedarwood | 4.7 A | 4.8 A | 3.4 A | 4.2 A | 1.1 B | 4.5 A | 1.0 B | 4.4 A | <0.0001*** |

Legend:
***= significant difference at 99.9%
**= significant difference at 99%
*= significant difference at 95%
= significant difference at 85% (tendency)

At step "Fresh", Composition B was significantly more intense in Rose and less intense in Tuberose notes; tended to be more intense in Bergamot and less intense in Aldehydic notes, in comparison to the Blank.

At step "After 2 h15 min", Composition B was significantly more intense in Bergamot, Freesia and Honeysuckle; tended to be more intense in Neroli, Aldehydic, Hyacinth, Musk, Hay, Cedarwood notes and less intense in Creamy notes, in comparison to the Blank.

Figure 3:
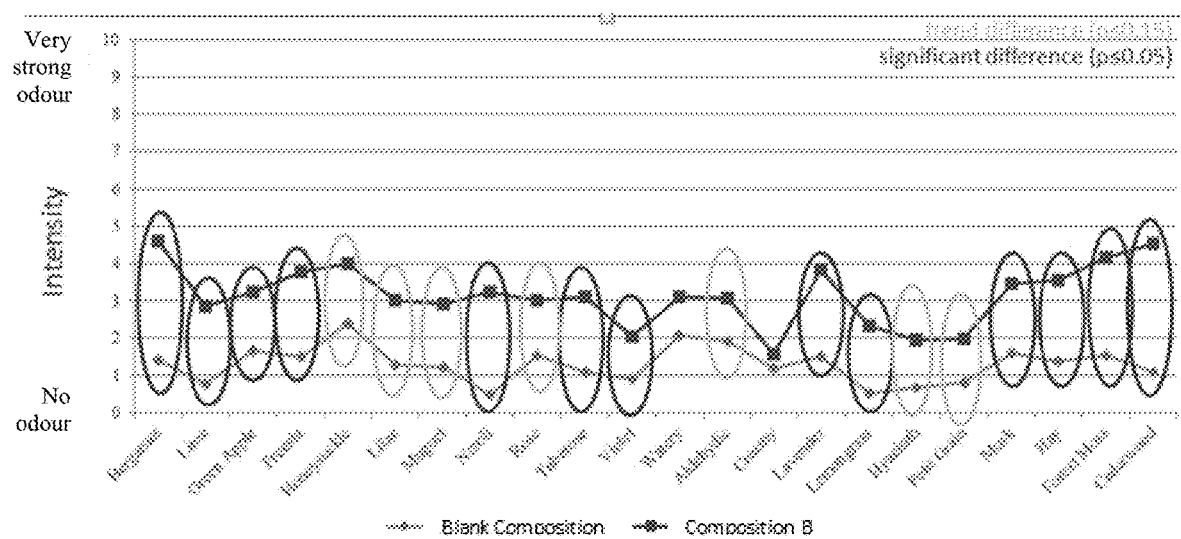
FIG. 3 is a graph that shows the perceived intensity of different notes for a composition according to the invention and for a blank composition—4 h15 after application—(dark circles represent a significant difference p≤0.05 and light circles represent a trend difference p≤0.15).
Figure 4:
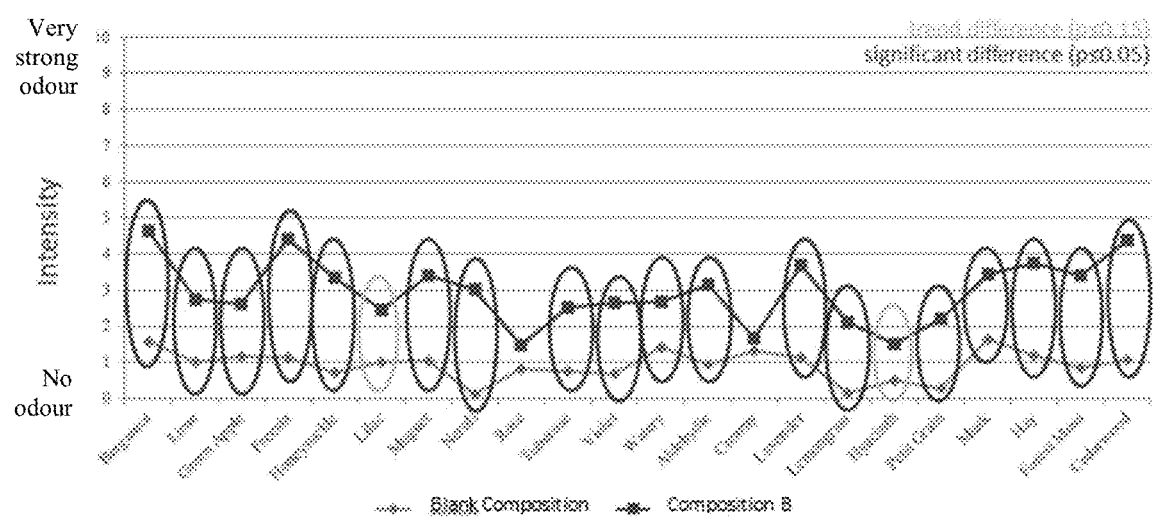
FIG. 4 is a graph that shows the perceived intensity of different notes for a composition according to the invention and for a blank composition—6 h15 after application—(dark circles represent a significant difference p≤0.05 and light circles represent a trend difference p≤0.15).

At step "After 4 h15 min", as shown in FIG. 3, composition B was significantly more intense in Bergamot, Lime, Green Apple, Freesia, Neroli, Tuberose, Violet, Lavender, Lemongrass, Musk, Hay, Forest Moss, Cedarwood; and tended to be more intense in Honeysuckle, Lilac, Muguet, Aldehydic, Hyacinth, Petit Grain, in comparison to the Blank.

At step "After 6 h15 min", as shown in FIG. 4, composition B was significantly more intense in most attributes, tended to be more intense in Lilac and Hyacinth, and was not significantly different in Rose and Creamy notes, in comparison to the Blank.

"After 4 h15 min" and "After 6 h15 min", the Blank has a relatively weak overall intensity, which lead to difficulty in perceiving and quantifying attributes, whereas Composition B could be easily described. The composition of the invention has a positive impact on olfactive profile of fragrance, increasing its noticeability and its longlastingness (since the overall intensity is perceived as relatively intense (typically intensity higher than 3.5) even 6 hours after application).

The invention claimed is:
1. An air freshener comprising:
a liquid composition, and
dispensing means to dispense fully into the air surrounding the air freshener the composition, wherein the liquid composition comprises:
i) a perfume and
ii) from 0.0005 to 0.2% by weight of the liquid composition of at least one compound according to Formula (IA)

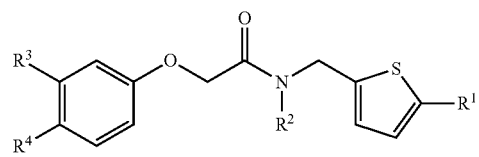

(IA)

wherein $R^1$ represents a hydrogen atom or a methyl group;
$R^2$ represents a pyrazol-5-yl or a pyrazol-4-yl, optionally substituted by one or two methyl groups;
$R^3$, when taken separately, represents a hydrogen atom and $R^4$, when taken separately, represents hydrogen atom or a methyl or methoxy group; or $R^3$ and $R^4$, when taken together, represent a $(CH_2)_3$ or $(OCH_2O)$ group;
wherein the air freshener is selected from the group consisting of an aerosol air freshener, an automatic aerosol air freshener spray and a liquid electrical air freshener.
2. The device according to claim 1, wherein $R^1$ represents a hydrogen atom.

3. The device according to claim 1, wherein $R^2$ represents a 1H-pyrazol-5-yl group.

4. The device according claim 1, wherein $R^3$, when taken separately, represents a hydrogen atom and $R^4$, when taken separately, represents a methyl group; or $R^3$ and $R^4$, when taken together, represent a $(CH_2)_3$ group.

5. The device according claim 1, wherein the at least one compound according to formula (IA) is N-(1H-pyrazol-5-yl)-N-(thiophen-2-ylmethyl)-2-(p-tolyloxy)acetamide.

6. The device according to claim 1, wherein the liquid composition to be dispensed comprises the perfume in an amount from 99.9995 and 99.0% by weight of the liquid composition.

7. The device according to claim 1, wherein the ratio between the perfume and the at least one compound according to formula (IA) is between 5000:1 and 50:1.

8. The device according to claim 1, wherein the liquid composition comprises 3,4-methylenedioxycinnamic acid, N,N-diphenylamide.

* * * * *